United States Patent
Williams, Jr. et al.

(10) Patent No.: US 9,228,220 B2
(45) Date of Patent: Jan. 5, 2016

(54) VALIDATION TECHNIQUES FOR FLUID DELIVERY SYSTEMS

(71) Applicant: Bracco Imaging S.p.A, Milan (IT)

(72) Inventors: Robert C. Williams, Jr., Fort Salonga, NY (US); Patrice Marchildon, Sea Cliff, NY (US)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 14/097,867

(22) Filed: Dec. 5, 2013

(65) Prior Publication Data

US 2014/0154671 A1    Jun. 5, 2014

Related U.S. Application Data

(60) Provisional application No. 61/733,825, filed on Dec. 5, 2012.

(51) Int. Cl.
*C12Q 1/22* (2006.01)
*C12Q 1/18* (2006.01)
(Continued)

(52) U.S. Cl.
CPC ... *C12Q 1/18* (2013.01); *A61L 2/18* (2013.01); *A61L 2/28* (2013.01); *A61M 5/00* (2013.01); *A61M 5/1408* (2013.01); *A61M 5/1413* (2013.01); *A61M 5/14232* (2013.01); *C12Q 1/22* (2013.01); *G01N 31/226* (2013.01); *G01N 33/50* (2013.01); *G01N 2013/003* (2013.01); *Y10T 436/13* (2015.01)

(58) Field of Classification Search
CPC .............. C12Q 1/18; C12Q 1/22; C12Q 1/04; G01N 31/22; G01N 31/226
USPC ......................................... 435/31, 32; 436/56
See application file for complete search history.

(56) References Cited

U.S. PATENT DOCUMENTS

| 4,292,405 A | 9/1981 | Mascoli et al. |
| 4,351,900 A | 9/1982 | Lemonnier |

(Continued)

FOREIGN PATENT DOCUMENTS

| EP | 1029526 B1 | 9/2004 |
| WO | 9310015 A1 | 5/1993 |

(Continued)

OTHER PUBLICATIONS

U.S. Appl. No. 14/308,468, title "Validation Techniques for Fluid Delivery Systems,", filed Jun. 18, 2014, 63 pages.

(Continued)

*Primary Examiner* — Jill Warden
*Assistant Examiner* — Dwayne K Handy
(74) *Attorney, Agent, or Firm* — Fredrikson & Byron, P.A.

(57) ABSTRACT

A fluid delivery system may include a container that houses a medical fluid, a fluid pressurizing unit, and a fluid transfer set that transfers the medical fluid from the container to the fluid pressurizing unit. To validate the integrity and sterility of the fluid delivery system, the system may undergo testing protocols to evaluate the susceptibility of the system to pathogenic ingress, chemical degradation, and/or fluid cross-contamination between patient fluid delivery procedures. The testing protocols may help ensure that delivery system components used during multiple different fluid delivery procedures perform as well as if the components were replaced after each fluid delivery procedure.

11 Claims, 11 Drawing Sheets

(51) Int. Cl.
*G01N 31/22* (2006.01)
*G01N 33/50* (2006.01)
*A61M 5/00* (2006.01)
*A61M 5/14* (2006.01)
*A61M 5/142* (2006.01)
*A61L 2/28* (2006.01)
*A61L 2/18* (2006.01)
*G01N 13/00* (2006.01)

(56) References Cited

U.S. PATENT DOCUMENTS

| | | | |
|---|---|---|---|
| 5,102,406 | A | 4/1992 | Arnold |
| 5,198,109 | A | 3/1993 | Hanson et al. |
| 5,310,094 | A | 5/1994 | Martinez et al. |
| 5,373,972 | A | 12/1994 | Bystrom et al. |
| 8,022,375 | B2 | 9/2011 | Williams et al. |
| 8,167,864 | B2 | 5/2012 | Browne |
| 8,210,166 | B2 | 7/2012 | Denton et al. |
| 2003/0072701 | A1 | 4/2003 | Lin et al. |
| 2005/0183495 | A1 | 8/2005 | Ichikawa et al. |
| 2008/0254471 | A1 | 10/2008 | Bordano |
| 2010/0130935 | A1 | 5/2010 | Hieb et al. |
| 2011/0061765 | A1 | 3/2011 | Hartman et al. |
| 2011/0208047 | A1 | 8/2011 | Fago |
| 2012/0108626 | A1 | 5/2012 | Hutchings et al. |
| 2012/0179130 | A1 | 7/2012 | Barnes et al. |
| 2013/0032545 | A1 | 2/2013 | Freese et al. |
| 2013/0109052 | A1 | 5/2013 | Yan et al. |
| 2014/0154670 | A1 | 6/2014 | Williams et al. |

FOREIGN PATENT DOCUMENTS

| | | | |
|---|---|---|---|
| WO | 9422412 | A1 | 10/1994 |
| WO | 2010118458 | A1 | 10/2010 |
| WO | 2014087247 | A2 | 6/2014 |

OTHER PUBLICATIONS

U.S. Appl. No. 14/308,489, title "Validation Techniques for Fluid Delivery Systems,", filed Jun. 18, 2014, 61 pages.

International Search Report for International Application No. PCT/IB2013/003163, mailed Jul. 29, 2014, 2 pages.

Christensen et al., "Assessment of risk of microbial contamination by use of multidose containers of injectable products", Journal of Hospital Infection, Apr. 1992, vol. 20, Issue 4, pp. 301-304. Abstract Only.

Frieben et al., "Integrity Testing of Vial Closure Systems Used for Parenteral Products", PDA Journal of Pharmaceutical Science and Technology, May-Jun. 1982, vol. 36, No. 3, pp. 112-116. Abstract Only.

Herts et al., "Power Injection of Contrast Media Using Central Venous Catheters: Feasibility, Safety, and Efficacy", American Journal of Roentgenology, Feb. 2001, vol. 176, No. 2, pp. 447-453.

Rathod et al., "Evaluation of the sterility and stability of insulin from multidose vials used for prolonged periods", American Journal of Infection Control, Dec. 1985, vol. 6, No. 12, pp. 491-494. Abstract Only.

US Pharmacopeial Convention, USP 35, Chapter 1, General Requirements "Injections", pp. 1-5. Retrieved Apr. 18, 2014 from: https://mc.usp.org/sites/default/files/documents/GeneralChapterPDFs/1_Injections.pdf.

E/M Associates, Inc., "Understanding USP <797> Compounding Sterile Preparations (CSP's)", White Paper, pp. 1-5, Retrieved Apr. 18, 2014 from: www.emassociates.net/Understanding USP 797.pdf.

Food and Drug Administration, "Summary of USP* 797—Pharmaceutical Compounding—Sterile Preparations", Pharmacopeial Forum—vol. 29 (4) Jul.-Aug. 2003, pp. 1-7.

American College of Radiology, "ACR Position Statement on Quality Control and Improvement, Safety, Infection Control, and Patient Education, (ACR Resolution 9, 1998—revised in 2008, Resolution 1e)", ACR Practice Guidelines and Technical Standards, pp. 1-2, Retrieved Apr. 18, 2014 from: http://www.acr.org/~/media/ACR/Documents/PGTS/PositionStatement.pdf.

International Search Report and Written Opinion for International Application No. PCT/IB2013/003163, mailed Oct. 27, 2014, 16 pages.

U.S. Appl. No. 14/308,468, Non-Final Office Action issued Dec. 12, 2014, 9 pages.

U.S. Appl. No. 14/308,468, Response to Non-Final Office Action filed Mar. 11, 2015, 8 pages.

U.S. Appl. No. 14/308,489, Non-Final Office Action issued Jan. 5, 2015, 7 pages.

U.S. Appl. No. 14/308,489, Response to Non-Final Office Action filed Apr. 2, 2015, 6 pages.

APPLY PATHOGEN — 200

DISINFECT COMPONENTS — 201

ASSEMBLE COMPONENTS — 202

DRAW FLUID THROUGH SYSTEM — 203

EXTRACT FLUID SAMPLE — 204

ANALYZE FLUID SAMPLE — 206

FIG. 5A

VALIDATION TECHNIQUES FOR FLUID DELIVERY SYSTEMS

CROSS-REFERENCE

This application claims priority to U.S. Provisional Patent Application No. 61/733,825, filed Dec. 5, 2012, the entire contents of which are incorporated herein by reference.

TECHNICAL FIELD

This disclosure relates to medical fluid containers and, more particularly, to medical fluid containers for medical fluid delivery systems.

BACKGROUND

Various medical procedures require that one or more medical fluids be injected into a patient. For example, medical imaging procedures oftentimes involve the injection of contrast media into a patient, possibly along with saline and/or other fluids. Contrast media can highlight features that would otherwise be less distinguishable from nearby tissue to help a clinician diagnose and treat a patient's medical condition. A patient is typically injected with contrast media before or during an imaging procedure and then exposed to radiation or electromagnetic energy to generate an image of the patient's body.

When used, contrast media is usually injected into a patient by an automated injection system. The automated injection system may include a pump, syringe, or other fluid delivery device operatively connected to a catheter. The catheter is placed into a vein or artery of a patient. During operation, the fluid delivery device operates to pressurize the contrast media and to inject the media into the patient at a predetermined rate and volume.

Contrast media for an automated injection system can be supplied in a container sized to provide multiple doses of contrast media to multiple different patients or a container sized to provide a single dose of contrast media to a single patient. For example, a powered syringe injector may use a pre-filled syringe that is filled with fluid at one facility and then shipped to another facility (e.g., an imaging suit) where it is installed on the powered injector. In this case, the syringe is used for a single injection on a single patient. Any contrast media remaining in the syringe after this single injection cannot be used for another patient and is thereby wasted.

Alternatively, a powered syringe injector may receive an empty syringe (e.g., in an imaging suite) that is filled with fluid from a multi-dose container in preparation for subsequent injection into a patient. The syringe in this application may or may not still only be used for a single injection on a single patient. However, the multi-dose container supplying fluid to the syringe and tubing connecting the container to the syringe may be used to fill multiple syringes for multiple different patients. Ensuring that contaminants do not enter the fluid supplied by the multi-dose container between syringe fillings or during syringe filling may be beneficial for the safe and efficient operation of the automated injection system.

SUMMARY

In general, this disclosure is directed to systems and techniques for evaluating the integrity and sterility of components in a fluid delivery system (e.g., a fluid injector system). The fluid delivery system includes, for example, a medical fluid container, a fluid pressurizing unit, and a fluid transfer set. The disclosed techniques can be used to help validate and ensure that the components of the fluid delivery system do not allow ingress of pathogens; do not chemically degrade during use; and/or do not allow cross-contamination of fluids between patients during subsequent injection procedures. By following structured protocols, suppliers of fluid delivery system components can benchmark their compliance and determine if redesign of injector system components is necessary. Further, fluid delivery system validation can allow suppliers, clinicians, and patients to all proceed with confidence in the knowledge that the injection system hardware meets standards for integrity.

In one example, a method is described that includes applying pathogen at a connection between a medical fluid container, a fluid pressurizing unit, and a fluid transfer set. The fluid transfer set is configured to provide fluid communication between the medical fluid container and the fluid pressurizing unit. The method also includes determining if the pathogen enters a medical fluid in at least one of the medical fluid container, the fluid pressurizing unit, and the fluid transfer set. Additionally, the method involves holding the medical fluid in the fluid transfer set and the fluid pressurizing unit, and evaluating the fluid to determine if chemical degradation has caused these components to release particles or leach chemicals into the medical fluid.

In another example, a method is described that includes applying a bacteria to a connection between a medical fluid container and a fluid transfer set, where the fluid transfer set is connected to transfer a fluid from the medical fluid container to a fluid pressurizing unit. The method also includes applying the bacteria to a connection between the fluid transfer set and the fluid pressurizing unit, and drawing the fluid from the medical fluid container, through the fluid transfer set, and into the fluid pressurizing unit. The example method further involves extracting a sample of the fluid from the fluid pressurizing unit, and analyzing the sample to determine a concentration level of the bacteria in the sample.

In another example, a method is described that includes providing a fluid delivery system that includes a medical fluid container, a fluid pressurizing unit, and a fluid transfer set, where the fluid transfer set is connected to transfer a fluid from the medical fluid container to the fluid pressurizing unit. The method includes drawing the fluid from the medical fluid container, through the fluid transfer set, and into the fluid pressurizing unit so that the fluid transfer set and fluid pressurizing unit are filled with the fluid, and holding the fluid in the fluid transfer set and the fluid pressurizing unit for a period of time. In addition, the method involves extracting a sample of the fluid from at least one of the fluid transfer set and the fluid pressurizing unit, analyzing the sample to determine if chemical degradation of the at least one of the fluid transfer set and the fluid pressurizing unit caused release of particles or leaching of chemicals into the sample.

In another example, a method is described that includes providing a fluid delivery system that includes a medical fluid container, a fluid pressurizing unit, and a fluid transfer set, where the fluid transfer set is connected to transfer a fluid from the medical fluid container to the fluid pressurizing unit. The method includes drawing the fluid from the medical fluid container, through the fluid transfer set, and into the fluid pressurizing unit so that the fluid transfer set and fluid pressurizing unit are filled with the fluid. Additionally, the method includes placing a discharge outlet of the fluid pressurizing unit in fluid communication with a fluid reservoir containing a tracking fluid, where the tracking fluid contains a tracking agent, and where the fluid reservoir is closed so that the fluid pressurizing unit cannot draw the fluid from the medical fluid container and discharge the fluid into the fluid reservoir. The example method further involves operating the fluid pressurizing unit so as to pressurize a portion of the fluid in the fluid pressurizing unit, extracting a sample of the fluid from at least one of the medical fluid container, the fluid transfer set, and the fluid pressurizing unit, and analyzing the sample to determine a concentration of the tracking agent in the at least one of the medical fluid container, the fluid transfer set, and the fluid pressurizing unit.

In another example, a method is described that includes providing a fluid delivery system that includes a medical fluid container, a fluid pressurizing unit having a discharge outlet, a fluid transfer set, and a discharge line. The fluid transfer set is connected to transfer a fluid from the medical fluid container to the fluid pressurizing unit, and the discharge line is connected to the discharge outlet of the fluid pressurizing unit. The method includes filling the discharge line with a tracking agent, establishing a positive pressure that biases the tracking agent in the discharge line toward the fluid pressurizing unit, and extracting a sample of the fluid from at least one of the medical fluid container and the fluid transfer set. The example method also includes analyzing the sample to determine a concentration of the tracking agent in the at least one of the medical fluid container and the fluid transfer set.

In another example, a method is described that includes applying a bacteria to a connection located between a medical fluid container and a fluid pressurizing unit, where a fluid transfer set is configured to transfer a fluid from the medical fluid container to the fluid pressurizing unit. The method includes operating the fluid pressurizing unit multiple times to discharge multiple portions of fluid from the fluid pressurizing unit and obtaining a plurality of samples from the multiple portions of fluid discharged from the fluid pressurizing unit, each of the plurality of samples being obtained from a different portion of fluid. The method also includes analyzing the plurality of samples to determine a concentration level of the bacteria in the plurality of samples.

Products validated using one or more method according to the disclosure are also described. For example, a validated kit may include a validated medical fluid container, a validated fluid transfer set, and/or a validated fluid pressurizing unit. The products may be validated for resistance to bacterial entry into a medical fluid held in the medical fluid container and transferred through the fluid transfer set via the fluid pressurizing unit. The products may additionally or alternatively be validated for chemical compatibility with a medical fluid. In one example, the medical fluid is a contrast medium.

The details of one or more examples are set forth in the accompanying drawings and the description below. Other features, objects, and advantages will be apparent from the description and drawings, and from the claims.

BRIEF DESCRIPTION OF DRAWINGS

FIGS. 5A, 5B, 6, 7A, and 7B are flow diagrams illustrating example techniques that may be performed to validate the integrity and sterility of the example fluid delivery system of FIG. 1.

DETAILED DESCRIPTION

Figure 1:
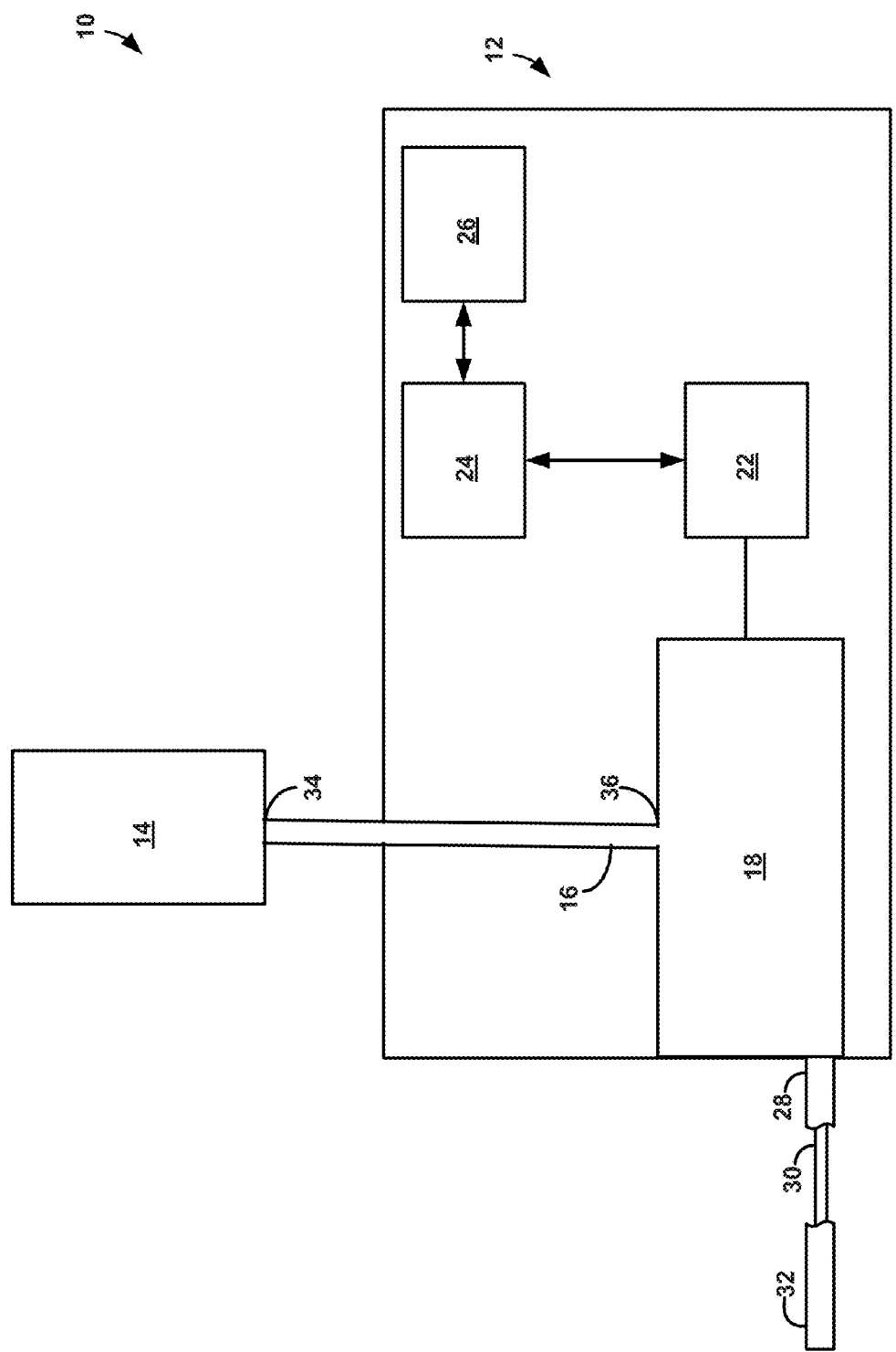
FIG. 1 is a function block diagram illustrating components of an example fluid delivery system.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes may be provided for selected elements, and all other elements employ that which is known to those of skill in the field of the invention. Those skilled in the art will recognize that many of the examples provided have suitable alternatives that can be utilized.

A powered medical fluid injector may be used to inject a medical fluid such as contrast media into the body of a patient during a diagnostic imaging procedure. To perform an injection, the medical fluid injector is supplied with one or more desired medical fluids. The medical fluid injector pressurizes the medical fluid and discharges the pressurized fluid into a catheter inserted into the patient. By controlling the type, rate, and volume of medical fluid delivered to the patient, a clinician can control the visual contrast of structures or fluids within the patient to help the clinician diagnose and treat the patient's medical condition.

A medical fluid injector can be supplied with medical fluid from a number of different sources. Depending on the configuration of the injector and type of fluid intended to be injected, the injector can be supplied with a single dose of fluid that is used only for a single patient. For example, when the medical fluid injector is configured as a syringe injector, a syringe prefilled with medical fluid by a medical fluid manufacturer or supplier may be loaded into the injector. After injecting the fluid from the syringe, the syringe may be removed and replaced with another prefilled syringe for a different patient. The empty syringe can be discarded or sent back to the medical fluid manufacturer or supplier for refilling and sterilization, as required.

Alternatively, rather than send a facility housing a medical fluid injector a syringe prefilled with fluid, a medical fluid manufacturer or supplier may instead send the facility a bulk container holding enough medical fluid for multiple patients. At the facility, personnel may connect the bulk container directly to the medical fluid injector or may instead connect the bulk fluid container to an injector reservoir (e.g., an empty syringe) that is filled and then loaded into the medical fluid injector. In either case, the bulk fluid container can supply enough medical fluid to inject multiple different patients with the fluid during different imaging procedures.

When a medical fluid injector is configured to receive fluid from a bulk medical fluid container, the injector can be connected to a multi-use tubing set that transfers the medical fluid from the container to the injector and a patient-specific tubing set that transfers the medical fluid from the injector to a specific patient. The multi-use tubing set may be used during injection procedures for multiple patients, although the tubing set may nevertheless be replaced on a periodic basis (for example, once per day or one per shift). The patient-specific tubing set, by contrast, may be replaced between patient injection procedures so that there is a new tubing set for each new patient.

Components used multiple times in a medical fluid injector system with different patients cannot become contaminated or lose sterility during any one injection procedure. This is because components contaminated or that have lost sterility during one injection procedure may cause cross-contamination between patients, compromising the integrity of the injection system. For example, if contaminants enter a bulk medical fluid container during an injection of one patient, the contaminants may remain in the fluid during injection of subsequent patients.

To help ensure that components used in a medical fluid injector system during multiple different injection procedures do not present a risk of cross-contamination between patients, the injector system and constituent components can be tested to validate their ability to resist cross-contamination and loss of sterility. For example, the injector system and constituent components may be tested prior to any patient injection procedures to validate that the system and components will not lose safety or integrity during the course of multiple different injection procedures.

In accordance with some examples of the present disclosure, systems and techniques are described for testing multi-use medical fluid injector system hardware to validate that the hardware does not become contaminated or otherwise lose chemical or biological safety or integrity during the course of injecting multiple different patients with medical fluid. The testing may validate that the multi-use hardware does not degrade during the course of multiple injection procedures and/or does not provide a pathway that can allow contaminants to enter the system and to transfer from one patient to another patient during expected use.

Example techniques for validating the safety and integrity of injector systems and their constituent components will be described in greater detail with reference to FIGS. 5-9. Further, example components that may be included in a medical fluid injector system will be described with reference to FIGS. 2-4. However, an example medical fluid delivery system will first be described with reference to FIG. 1.

FIG. 1 is a function block diagram illustrating components of a fluid delivery system 10, which includes a powered fluid injector 12, a medical fluid container 14 (hereinafter "container 14"), and a fluid transfer set 16 fluidly connecting powered fluid injector 12 to medical fluid container 14. Powered fluid injector 12 includes a fluid pressurizing unit 18, a motor 22, a processor 24, and a memory 26. Motor 22 is operatively coupled to fluid pressurizing unit 18 and configured to drive the fluid pressurizing unit to draw a medical fluid from container 14 and pressurize the fluid for discharge into a patient during an imaging procedure. Processor 24 is communicatively coupled to motor 22 and memory 26. In the example of FIG. 1, fluid pressurizing unit 18 defines a discharge outlet 28 that in fluid communication with a patient catheter 32 via a patient line or extension tube 30.

Fluid delivery system 10 may include one or more multi-use components that are used repeatedly during the course of multiple patient injections. For example, container 14 and fluid transfer set 16 may be used during the course of multiple patient injections and may only be replaced on a periodic basis. By contrast, one or more other components of fluid delivery system 10 may be patient-specific, single use components that are replaced for each patient injection procedure. For example, patient line 30 and catheter 32 may be replaced for each new patient receiving an injection using powered fluid injector 12. Fluid pressurizing unit 18 in powered fluid injector 12 may or may not also be replaced for each new patient.

In instances in which fluid delivery system 10 includes one or more multi-use components, the multi-use components cannot lose their integrity or provide pathways for contamination during their service life in the fluid delivery system. Testing the components in fluid delivery system 10 can validate the safety and integrity of the components for extended service during multiple injection procedures for multiple patients. Although different tests can be performed, in one example as will be described in greater detail below, the components are tested by challenging the connection or joints between components with a pathogen (e.g., bacteria and/or virus) and then evaluating whether the pathogen is able to enter a medical fluid in fluid delivery system 10 at the connection or joints. In another example, the components of fluid delivery system 10, including fluid transfer set 16 and pressurizing unit 18, are filled with a medical fluid that is then allowed to reside in the components for a period longer than components would be filled during a single patient injection. The medical fluid and/or components are then evaluated to determine if the components degrade and release particles or leach chemicals into the medical fluid. In yet another example, pressurizing unit 18 is operated to discharge medical fluid against a blocked fluid outlet containing a tracking agent. Such an operation may simulate injecting medical fluid into a patient with a blocked catheter. Additionally or alternatively, a discharge line connected to pressurizing unit 18 may be filled with a tracking agent and placed under a pressure that tends to force the tracking agent back into the pressurizing unit. In either example, a medical fluid in fluid communication with pressurizing unit 18 during testing with the tracking agent can be evaluated to determine if the tracking agent is present in the medical fluid, which may indicate backflow of fluid from a patient-specific line into a multi-use component. In this way the operational integrity of fluid delivery system 10 may be analyzed and validated.

During operation of powered fluid injector 12, pressurizing unit 18 receives a medical fluid from container 14, pressurizes the medical fluid, and discharges the pressurized medical fluid through discharge outlet 28 and into catheter 32. Pressurizing unit 18 can be any mechanism configured to increase the pressure of a liquid medical fluid for injection into a patient. Depending on the configuration of pressurizing unit 18, the unit may pressurize the medical fluid so it discharges through discharge outlet 28 at a pressure greater than 50 pounds per square inch (psi) such as, e.g., a pressure greater than 200 psi, a pressure greater than 500 psi, or even a pressure greater than 1000 psi.

In one example, pressurizing unit 18 is implemented as a syringe. The syringe may include a syringe barrel that receives and holds medical fluid from container 14 and a plunger that is disposed within and moveable relative to the syringe barrel. To fill the syringe, the syringe may be fluidly coupled to container 14 and the syringe plunger driven to its furthest forward position adjacent discharge outlet 28. This will expel the majority of the air that is located within the syringe. Thereafter, the plunger is retracted within the syringe barrel, creating a vacuum within the syringe barrel that draws medical fluid from container 14 and into the syringe barrel. To subsequently discharge the medical fluid, fluid communication between the syringe barrel and container 14 is closed, and the plunger is advanced forward in the syringe barrel to pressurize and discharge the medical fluid in the syringe barrel.

In another example, pressurizing unit 18 is implemented as a pump. The pump may draw fluid from container 14 and discharge the fluid under an increased pressure out of discharge outlet 28. When pressurizing unit 18 is implemented as a pump, the pump may be an axial pump, a centrifugal pump, a pusher plate pump, a piston-driven pump, or other pumping device. In one such example (e.g., FIGS. 8A, 8B, and 9), the pump is a squeeze pump that squeezes a compressible fluid tube (e.g., a plastic tube) in a controlled manner, e.g., such as a peristaltic pump, to progressively pressurize and move medical fluid through the tube.

While powered fluid injector 12 in the example of FIG. 1 is illustrated as having only a single pressurizing unit 18, in other examples, the powered injector system may have multiple pressurizing units. For example, in addition to pressurizing unit 18 receiving fluid from container 14, powered fluid injector 12 may include one or more additional pressurizing units that can receive fluid from container 14 or a different medical fluid container (not illustrated). For instance, powered fluid injector 12 may include pressurizing unit 18 that receives fluid from container 14 holding one type of medical fluid and another pressurizing unit that receives fluid from a different container holding a different type of medical fluid. When powered fluid injector 12 includes multiple pressurizing units, each pressurizing unit may be the same type (e.g., each pressurizing unit is a syringe or pump) or the pressurizing units may be of different types.

Motor 22 is operatively coupled to pressurizing unit 18 and may provide mechanical energy that causes the pressurizing unit to draw medical fluid from container 14 and to pressurize the medical fluid for discharge out through discharge outlet 28. In one example, motor 22 is a DC motor that is configured to advance and retract a plunger through a syringe barrel. In another example, motor 22 is a DC motor that is configured to drive a pump head. Regardless, motor 22 may or may not be a variable speed motor that can ramp up speed and ramp down speed to control the rate at which pressurizing unit 18 delivers medical fluid to a patient.

During operation, powered fluid injector 12 receives medical fluid from container 14. Container 14 may be a bottle, a bag, or any other suitable container that is configured to hold and store a liquid fluid. Container 14 is typically formed from plastic or glass, although any suitable materials can be used to fabricate container 14. Depending on the application, container 14 may be sized to hold enough liquid to inject only a single dose of the liquid into a single patient or enough liquid to inject multiple doses of the liquid into multiple different patients. When container 14 is sized to hold only a single dose of liquid for a single patient, the container may, for example, hold a volume less than approximately 100 milliliters (ml). By contrast, a container sized to hold enough liquid to inject multiple doses of the liquid into multiple different patients may hold more liquid that fluid pressurizing unit 18 can hold when fully filled. In some examples when container 14 is sized to hold enough liquid to inject multiple doses, the container may hold greater than approximately 100 ml such as, e.g., greater than or equal to 200 ml, greater than or equal to 300 ml, or greater than or equal to 500 ml. The foregoing volumes are merely examples, and it should be appreciated that the disclosure is not limited in this respect.

Container 14 can contain a wide variety of different fluids such as contrast media, flushing agents (e.g., saline), and fluid medications, among others. Contrast media is a liquid that can be injected into a patient to highlight selected areas of the patient while the patient is being scanned, e.g., radiographically. Contrast media typically has a viscosity ranging from approximately 1 centipoise to approximately 50 centipoise and, in some examples, may have an organically (i.e., non-ionic) or non-organically (i.e., ionic) bound molecule that functions to provide contrast, such as organically or non-organically bound iodine. Examples of iodine-based contrast media include diatrizoate (Hypaque™ 50), metrizoate (Isopaque 370), ioxaglate (Hexabrix), iopamidol (Isovue® 300, Isovue® 370), iohexol (Omnipaque™ 350), ioxilan (Oxilan® 350), iopromide (Ultravist® 370), and iodixanol (Visipaque™ 320). Other example contrast media agents include barium-based agents such as barium sulfate. In still other examples, contrast media may include gadolinium for MR imaging, radioisotopes for nuclear medicine, micro-spheres for ultrasound, or the like.

Although fluid delivery system 10 is only illustrated as including a single container 14 of medical fluid, fluid delivery system 10 may include multiple containers that can each house the same medical fluid or that can house different medical fluids. In one example, fluid delivery system 10 includes at least two containers that each house the same contrast medium, increasing the amount of fluid connected to pressurizing unit 18 for injecting into patients as compared to when there is only a single reservoir. In another example, fluid delivery system 10 includes at least two containers where one container houses a contrast medium and another container houses a flushing media such as saline. Powered fluid injector 12 may inject alternating doses of the contrast medium and the saline into a patient to control the patient's response to the contrast medium during imaging.

To transfer medical fluid from container 14 to pressurizing unit 18, fluid delivery system 10 includes fluid transfer set 16. Fluid transfer set 16 may provide a fluid communication pathway between container 14 and pressurizing unit 18. Fluid transfer set 16 may include a segment of tubing (e.g., flexible polymeric tubing) or duct that allows fluid to be conveyed from container 14 to fluid pressurizing unit 18. In the illustrated example, fluid transfer set 16 extends from a proximal end 34 that connects to container 14 to a distal end 36 that connects to pressurizing unit 18. In such an example, fluid transfer set 16 may define at least one connection between the fluid transfer set and container 14 and another connection between the fluid transfer set and pressurizing unit 18. The connections may be locations where one component (e.g., container 14) is joined to another component (e.g., a flexible tube) to form a junction. The specific number of connections between container 14 and pressurizing unit 18 may vary depending on the specific configuration of fluid transfer set 16. Further, depending on the configuration, each of the connections may be detachable connections rather than permanent connections to allow an operator to exchange and replace components. In addition, depending upon the design of fluid injector 12, transfer set 16 may interface with an ultrasonic or electro-optic sensor to detect fluid presence in the tube. This can serve the dual purpose of preventing air entry into the pressurizing unit by allowing the operator to have an automatic container 14 empty detection.

To connect proximal end 34 of fluid transfer set 16 to container 14, the fluid transfer set may have a mechanical connector positioned at proximal end 34. The mechanical connector may be a threaded male or female connector that is configured to mate with a corresponding connector on container 14. For example, fluid transfer set 16 may have a female or male luer lock fitting positioned at proximal end 34 that is configured to engage with a corresponding luer lock fitting on container 14 for creating a fluid tight connection between the components. Alternatively, as described with respect to FIG. 4, fluid transfer set 16 may have a bottle spike positioned at proximal end 34 for piercing a seal on container 14 when placing the container in service.

Distal end 36 of fluid transfer set 16 may also have a mechanical connector for connecting to pressurizing unit 18. For example, as with the connector on proximal end 34, the mechanical connector on distal end 36 may be a threaded male or female connector that is configured to mate with a corresponding connector on container 14. In one example, fluid transfer set 16 has a female or male luer lock fitting positioned at distal end 36 that is configured to engage with a corresponding luer lock fitting on pressurizing unit 18 for creating a fluid tight connection between the components. In addition, although distal end 36 of fluid transfer set 16 is described as connecting to pressurizing unit 18, it should be appreciated that the fluid transfer set may not connect to the pressurizing unit directly but may instead connect through intermediary structures. For example, distal end 36 of fluid transfer set 16 may connect to a valve assembly that controls fluid communication between container 14 and pressurizing unit 18 which, in turn, is in fluid communication with the pressurizing unit.

In the example of FIG. 1, pressurizing unit 18 is simultaneously connected to container 14 and catheter 32 through separate fluid ports. In other examples, pressurizing unit 18 may have a single fluid port that is connected at separate times to container 14 and catheter 32. For example, during a fill operation, pressurizing unit 18 may be connected to container 14. Once pressurizing unit 18 has been filled with a suitable amount of fluid, the pressurizing unit may be disconnected from container 14 and connected to catheter 32, thereby allowing a single fluid port to function as both a fluid filling inlet and a fluid discharge outlet.

During operation of powered fluid injector 12, processor 24 may control the filling of medical fluid to and discharge of medical fluid from pressurizing unit 18 with the aid of instructions associated with program information stored in memory 26. Processor 24 may also control the filling of medical fluid to and discharge of medical fluid from pressurizing unit 18 based on instructions received from a user, e.g., via a user interface. Instructions executed by processor 24 may, for example, define fluid delivery programs that specify the quantity, rate, and/or pressure with which medical fluid is to be delivered from pressurizing unit 18 through discharge outlet 28 during a diagnostic imaging procedure and/or during operational testing of powered fluid injector 12. Instructions executed by processor 24 may also control the opening and closing of valves within fluid delivery system 10 (not illustrated) to fill pressurizing unit 18 with medical fluid and to discharge the fluid from the unit.

Processor 24 may include one or more processors, such as one or more microprocessors, digital signal processors (DSPs), application specific integrated circuits (ASICs), field programmable gate arrays (FPGAs), programmable logic circuitry, or the like, either alone or in any suitable combination. In general, processor 24 may receive electrical signals from input devices such as a user interface and provide electrical signals to output devices such as motor 22. For example, processor 24 may provide signals to motor 22 to control the advancing and retracting of a plunger in a syringe barrel and/or the movement of a pump head. Memory 26 may store instructions and related data that, when executed by processor 24, cause powered fluid injector 12 and processor 24 to perform the functions attributed to them in this disclosure. Typically, powered fluid injector 12 uses electrical energy to drive pressurizing unit 18, although hydraulic, pneumatic, or other suitable power sources may also be used.

In the example of FIG. 1, fluid pressurizing unit 18 defines a discharge outlet 28 that is in fluid communication with a patient catheter 32 via a patient line 30. Patient line 30 may also be referred to as a discharge line, e.g., when the line is not connected to catheter 32 outside of a patient injection procedure. Discharge outlet 28 may be an opening in fluid pressurizing unit 18 through which high pressure fluid is discharged and may or may not include a length of tubing (e.g., patient line 30 or another line) connected to the outlet. Patient line 30 may be a length of tubing that traverses from powered fluid injector 12 to catheter 32 and can comprise a unitary tube or a plurality of tube segments connected together to form an overall length of tube. In other examples, catheter 32 may be coupled directly to fluid pressurizing unit 18 without the aid of intermediate tubing or extensions.

Fluid delivery system 10 can be used in any appropriate application where delivery of one or more medical fluids is desired including, for example, during any type of medical imaging procedure. Example imaging procedures in which fluid delivery system 10 can be used include, but are not limited to, X-ray, computed tomography (CT), nuclear magnetic resonance (NMR)/magnetic resonance (MR), ultrasound, fluoroscopy, and positron emission tomography (PET). When used in these applications, powered fluid injector 12 may be communicatively coupled to an imaging system (e.g., a CT scanner) and may send and receive electrical signals between the imaging system for controlling the operation of the fluid delivery device.

Figure 2:
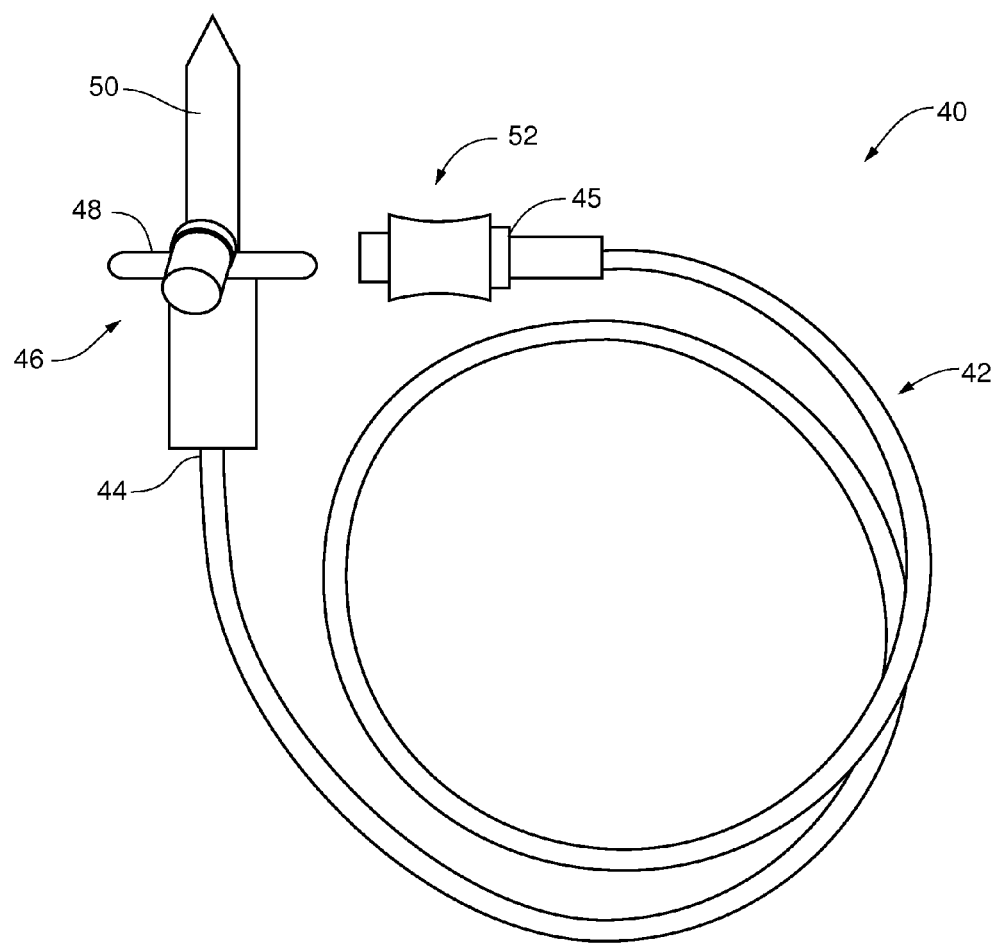
FIG. 2 is an illustration of an example configuration of a fluid transfer set that may be used in the example fluid delivery system of FIG. 1.

As discussed above, fluid delivery system 10 can have a variety of different configurations to transfer fluid from container 14 to fluid pressurizing unit 18 and, ultimately, catheter 32. FIG. 2 illustrates one example configuration of a fluid transfer set 40 that may be used as fluid transfer set 16 in fluid delivery system 10. Fluid transfer set 40 includes a length of flexible polymeric tubing 42 that extends from a proximal end 44 to a distal end 45. A mechanical connector 46 is located at proximal end 44 and is configured to mate with container 14 so as to create a fluid tight connection between the container and fluid transfer set 40. Mechanical connector 46 includes a base 48 that is configured to receive and mate with a rim of container 14 that extends around an opening through which medical fluid is withdrawn from the container. Mechanical connector 46 also includes a spike 50 that projects proximally away from base 48. As described in greater detail with respect to FIG. 4, spike 50 is configured to be inserted into container 14 and to pierce a seal on the container so as to place the container in fluid communication with fluid transfer set 40.

Fluid transfer set 40 in the example of FIG. 2 also includes a mechanical connector 52 located at distal end 45 of tubing 42. Mechanical connector 52 in this example is a luer lock fitting that is configured to mate with a corresponding luer lock fitting on fluid pressurizing unit 18 (FIG. 1) so as to create a fluid tight connection between the fluid pressurizing unit and fluid transfer set 40. In some applications in accordance with this example, the fluid pressurizing unit is a syringe.

To place fluid transfer set 40 in service, an operator may insert bottle spike 50 into container 14 and secure the container to base 48 so that there is a connection between the container and proximal end 44 of the fluid transfer set. The operator may further engage the luer lock fitting 52 with a corresponding luer lock fitting on pressurizing unit 18 so that there is a connection between the pressurizing unit and distal end 45 of the fluid transfer set. In this manner, fluid communication can be established between container 14 and fluid pressurizing unit 18 using a fluid transfer set that defines two connection locations. Container 14, fluid transfer set 40 and, in some examples, pressurizing unit 18 may be used repeatedly during multiple injection procedures to transfer medical fluid from a multi-dose container to a pressurizing unit.

Figure 3:
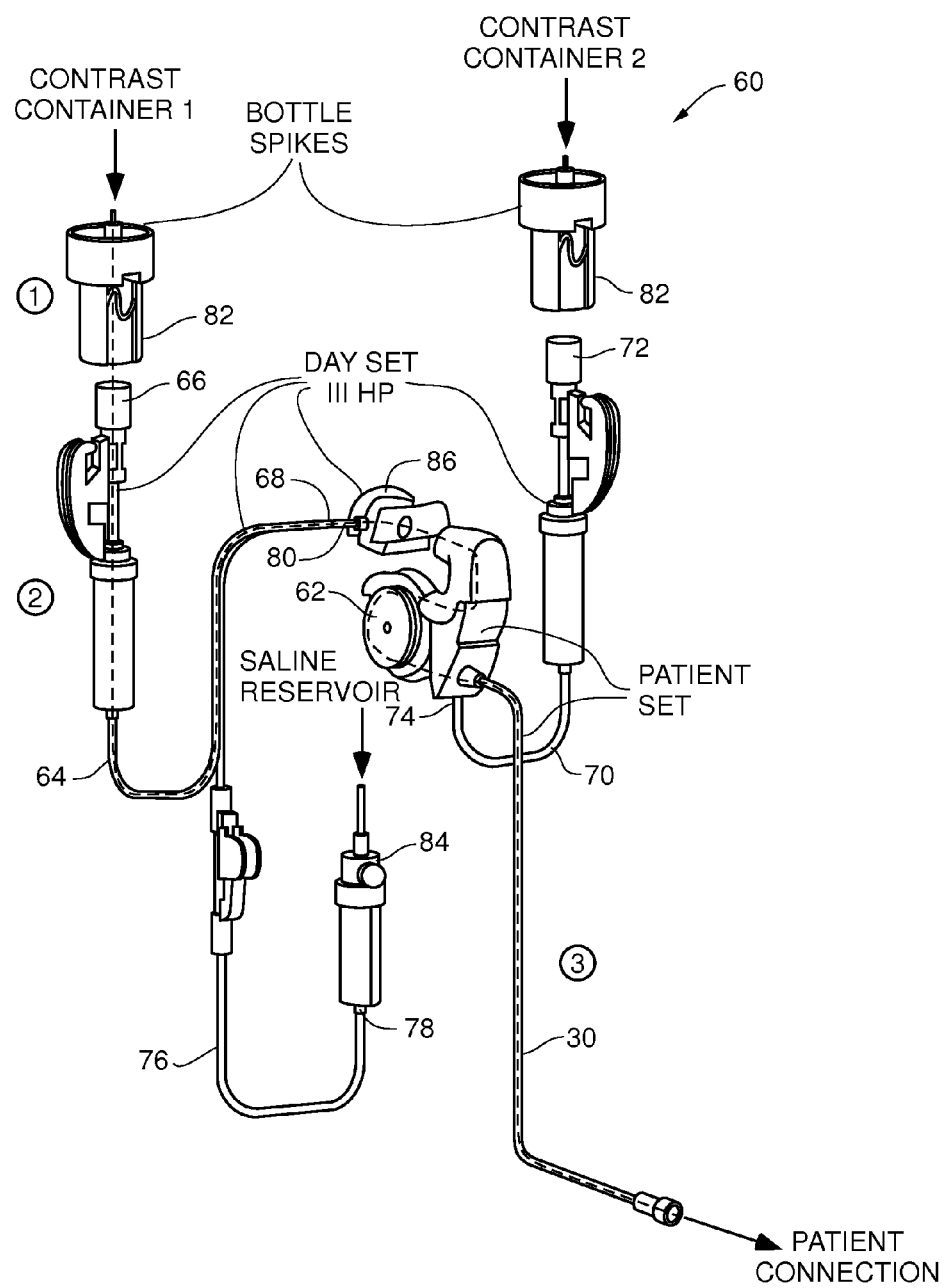
FIG. 3 is an illustration of another example configuration of a fluid transfer set that may be used in the example fluid delivery system of FIG. 1.

FIG. 3 is an illustration of another example configuration of a fluid transfer set 60 that may be used in fluid delivery system 10. Fluid transfer set 60 is configured to fluidly connect at least one container 14 (FIG. 1) to fluid pressurizing unit 18. In the illustrated example of FIG. 3, fluid transfer set 60 is configured to connect three containers to a fluid pressurizing unit 62 that is shown as a peristaltic pump. Fluid transfer set 60 includes a first length of flexible polymeric tubing 64 that extends from a proximal end 66 to a distal end 68, a second length of flexible polymeric tubing 70 that extends from a proximal end 72 to a distal end 74, and a third length of flexible polymeric tubing 76 that extends from a proximal end 78 to a distal end 80. The first and second lengths of tubing 64 and 70 may each fluidly connect a container of contrast media to pump 62. The third length of tubing 76 may fluidly connect a container of saline to pump 62.

In the example of fluid transfer set 60, proximal end 66 of first tubing 64 and proximal end 72 of second tubing 70 are each connected to a mechanical connector 82 that is configured to mate with a container so as to create a fluid tight connection between the container and the fluid tubing. Third tubing 76 also has a mechanical connector 84 that is configured to mate with a container holding saline so as to create a fluid tight connection between the container and fluid tubing. At the opposite end, first tubing 64 and third tubing 76 are each connected at their distal ends to a fluid pressurizing unit inlet connector 86 (e.g. a pump inlet connector). Fluid pressurizing unit inlet connector 86 is configured to mate with a fluid pressurizing unit (e.g., pump 62) so as to create a fluid tight connection between the connector and the pump. Second fluid tubing 70 is connected directly to pump 62 and, in different examples, may be connected upstream of the pump so that fluid from the tubing is pressurized within the pump or downstream of the pump so that fluid from the tubing bypasses pressurization within the pump.

To place fluid transfer set 60 in service, an operator may connect mechanical connectors 82 to first and second tubing 64 and 70 and further connect mechanical connectors 82 and 84 to corresponding containers filled with medical fluid(s). The operator may further connect fluid pressurizing inlet connector 86 to an inlet of pump 62, thereby establishing fluid communication between the first and third tubing 64 and 76 and pump 62. Second tubing 70 may be connected to fluid pressurizing inlet connector 86 or may have a separate mechanical connector that an operator separately connects to pump 62. When assembled, fluid communication may be established between two containers holding contrast media, one container holding saline, and pump 62. Fluid transfer set 60 may define connections at least between mechanical connectors 82 and first and second tubing lines 64 and 70, a connection between fluid pressurizing unit inlet connector 86 and pump 62, and a connection between second tubing 70 and pump 62. First tubing line 64, second tubing line 70, and third tubing line 76 along with the containers to which the tubing is connected may be used repeatedly during multiple injection procedures to transfer medical fluid from the containers to pump 62. Pump 62 and a patient line or discharge line 30 to which a discharge outlet of the pump is connected may be replaced for each patient and/or each injection procedure.

Figure 4:
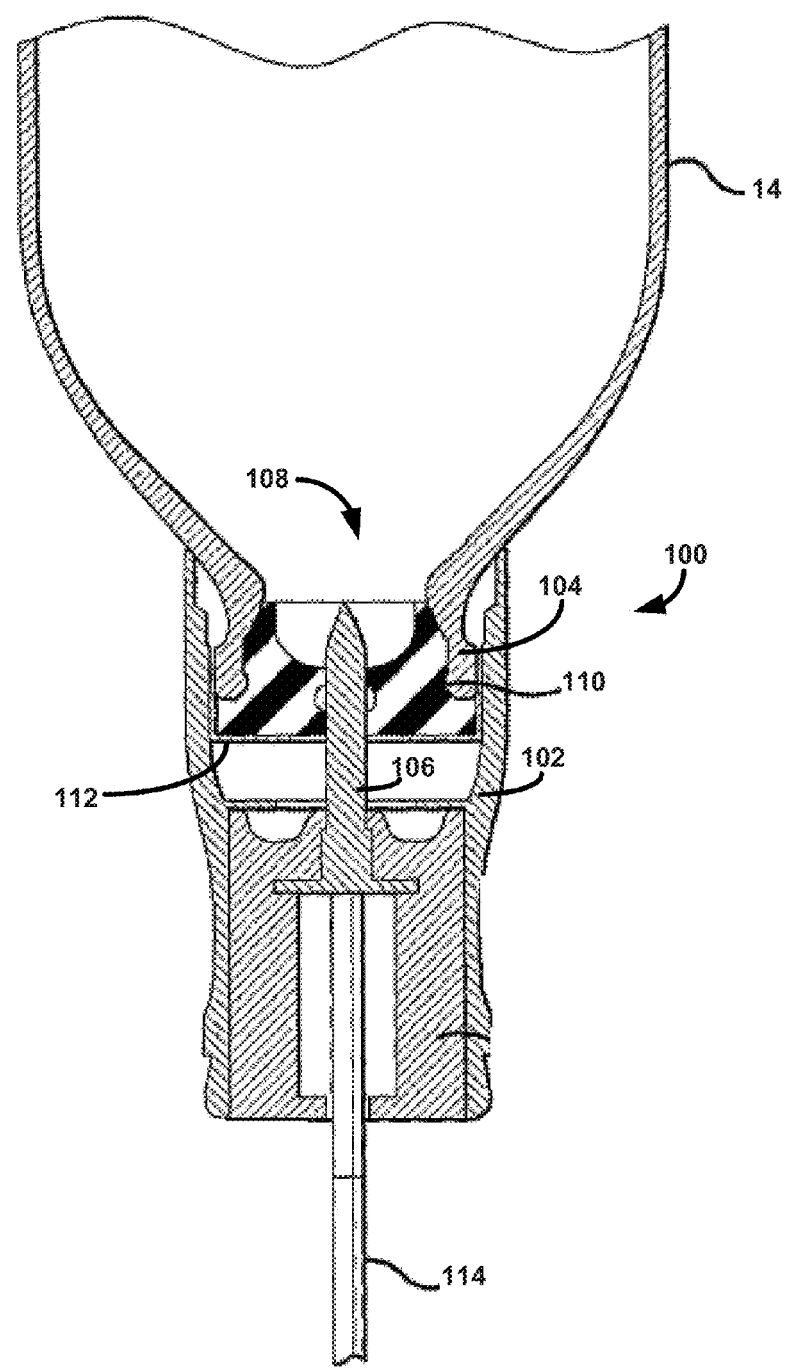
FIG. 4 is a cross-sectional illustration of an example mechanical connector that can be used in the example fluid delivery system of FIG. 1.

FIG. 4 is a cross-sectional illustration of an example mechanical connector 100 that can be used in fluid delivery system 10 (FIG. 1) to connect a tubing line to container 14 housing a medical fluid. Mechanical connector 100 defines a base 102 that is configured to be positioned around rim 104 of the container 14 so that fluid does not leak out between the connector and the container. Mechanical connector 100 also includes a spike 106 that is inserted into an aperture 108 defined by rim 104. Spike 106 may pierce a seal that extends over aperture 108 to close and hermetically seal the container, e.g., for shipping and storage prior to use. In the illustrated example, spike 106 pierces a seal that includes a septum 110 and a foil or collar 112. When spike 106 pierces septum 110 and foil/collar 112 to access an interior of container 14, tubing 114 is placed in fluid communication with the contents of the container and can receive and convey the contents, e.g., to fluid pressurizing unit 18.

To help ensure that the various components of fluid delivery system 10 (FIG. 1) do not lose their physical integrity or provide pathways that allow contaminants to enter a sterile medical fluid during the course of use, fluid delivery system 10 may be tested to evaluate and validate the integrity of the system. For example, if fluid delivery system 10 were to be used to transfer medical fluid from container 14 to fluid pressurizing unit 18 in a non-sterile environment (e.g., in an imaging suite), the fluid delivery system may be validated to help ensure the system will be safe and sterile during the course of service.

FIGS. 5A-5B, 6, and 7A-7B, are flow diagrams illustrating example techniques that may be performed to validate the integrity and sterility of a medical fluid delivery system including, e.g., components of the system that may be used multiple times during multiple different patient injection procedures. For ease of description, the techniques of FIGS. 5-7 will generally be described with reference to fluid delivery system 10 in FIG. 1. The techniques can be performed on fluid delivery systems having other configurations, as described herein, and it should be appreciated that the techniques are not limited to the example fluid delivery system of FIG. 1.

In addition, in practice, the techniques of FIGS. 5A-5B, 6, and 7A-7B can be executed in a number of different environments. In one example, the techniques are performed in a cleanroom to help prevent external contaminants from entering medical fluids during testing. In another example, the techniques are performed under a laminar flow air hood, again to help prevent external contaminants from entering medical fluids during testing. Other locations for performing the techniques are also possible.

With reference to FIG. 5A, the example technique includes applying one or more pathogens (e.g., one or more viruses and/or bacteria) to one or more components in fluid delivery system 10 (200). For example, a user may apply the pathogen by rubbing or brushing a culture containing the pathogen on the one or more components or by immersing the components in a culture containing the pathogen. By applying the pathogen to the one or more components, a user may determine the ability of fluid delivery system 10 to resist the passage of microorganisms into fluid pathways that convey medical fluid from container 14 to a patient during an injection procedure.

In some examples, the pathogen is applied at a connection between different components in fluid delivery system 10. The connection, which is where different components are detachably joined, may provide the most likely pathway through which the pathogen could enter a medical fluid in the system. For example, the pathogen may be applied at a connection (e.g., all connections) between container 14 and fluid transfer set 16 and/or a connection (e.g., all connections) between fluid transfer set 16 and fluid pressurizing unit 18. In different examples, the pathogen is applied after the components are joined together to test whether external contamination of joined components can enter a medical fluid or before the components are joined together to test whether external contamination of components before joining can allow the contamination to enter the medical fluid.

When fluid transfer set 16 is configured in the example of FIG. 2, for instance, the pathogen may be applied to mechanical connector 46 and/or container 14 (e.g., a seal covering the container) before the components are joined together. The pathogen may be applied to external surfaces of mechanical connector 46 and/or container 14 that would be touched by an operator during normal use. A user may subsequently insert spike 50 of mechanical connector 46 into container 14 to fluidly connect the fluid transfer set to the container. Alternatively, mechanical connector 46 may be mated with container 14 to define a fluid tight connection between the two components and, thereafter, the pathogen applied at the junction where the two components mate.

In addition to or in lieu of applying the pathogen to mechanical connector 46 and/or container 14, the pathogen can be applied to mechanical connector 52 and/or fluid pressurizing unit 18. In one example, the pathogen is applied to external surfaces of mechanical connector 52 and/or fluid pressurizing unit 18 that would be touched by an operator during normal use. For example, the pathogen may be applied around the external surface of a luer lock fitting and/or at an inlet of a syringe barrel or fluid pump. A user may subsequently mate mechanical connector 52 with a corresponding connector on fluid pressurizing unit 18 to fluidly connect the fluid transfer set to the fluid pressurizing unit.

As another example, specifically when fluid transfer set 16 is configured as shown in the example of FIG. 3, the pathogen may be applied to mechanical connectors 82, 84 and/or the containers to which the connectors join, as described above with respect to the fluid transfer set of FIG. 2. The pathogen may be applied to mechanical connectors 82, 84 and/or the containers to which the connectors join before mating the connectors with the containers or after mating the connectors with the containers. In addition to or in lieu of applying the pathogen to the mechanical connector and/or containers, the pathogen can be applied at one or more connections where tubing mates with pump 62. For example, the pathogen may be applied on external surfaces of fluid pressurizing unit inlet connector 86 and/or an inlet of pump 62 to which the connector mates before or after the components are mated together.

The type and amount of pathogen applied at connection locations and/or to components within fluid delivery system 10 may vary, e.g., based on the severity and parameters of testing. When bacteria is used as the pathogen, example bacteria that may be applied include, but are not limited to, *Staphylococcus aureus*, *Staphylococcus epidermidis*, *Pseudomanas aeruginosa*, *Klebsiella pneumonia*, *Escherichia coli*, *Candida albicans*, and *Aspergillus niger*. In some examples, multiple types of bacteria are applied to fluid delivery system 10, for example either simultaneously together or by conducting serial tests using one type of bacteria and then another type of bacteria, to evaluate the ability of fluid delivery system 10 to resist the passage of different types of microorganisms. In one example, at least 100 colony forming units/milliliter (CFU/ml) of bacteria are applied to each component or connection location during the technique of FIG. 5A such as, e.g., at least 500 CFU/ml, at least 1000 CFU/ml, or at least 5000 CFU/ml. Bacteria applied to fluid delivery system 10 may be in an organism diluent, such as Mile's Test Soil or Tryptic Soy Broth.

In applications where the pathogen is applied to the components of fluid delivery system 10 prior to assembly, the components may subsequently be disinfected (201) and assembled (202) to place the components in fluid communication with one another. Disinfecting the components of fluid delivery system 10 prior to assembly may remove surface pathogens from the components so that the pathogens are not deliberately introduced into medical fluid during assembly of the components. For example, by applying the pathogen to one or more components of fluid delivery system 10 and then disinfecting the surfaces of the components, the technique of FIG. 5A may be used to determine whether the pathogen bypassed a seal or barrier of the components (e.g., a seal covering a medial fluid container) or otherwise invaded the components such that surface disinfection does not remove the pathogen.

To disinfect the one or more components of fluid delivery system 10 (201), a disinfectant designed to kill and/or remove the pathogen can be applied to surfaces of the components where the pathogen was originally applied. An example disinfectant is an isopropyl alcohol solution (e.g., containing greater than 60% isopropyl alcohol such as approximately 70% isopropyl alcohol), although other disinfectants can be used. The disinfectant can be applied to or impregnated in a cloth that is then wiped over the surfaces of the components. In some examples, the cloth is wiped over a surface of a component so that the cloth is in contact with the component for a period of time greater than 5 seconds such as, e.g., a period greater than 20 seconds, a period greater than 30 seconds, or a period of time ranging from approximately 25 seconds and approximately 30 seconds.

When fluid transfer set 16 is configured in the example of FIG. 2, for instance, mechanical connector 46 and/or container 14 (e.g., a seal covering the container) may be disinfected by wiping a cloth containing a disinfectant over the surfaces of the mechanical connector and/or container to which the pathogen was applied. As another example, when fluid transfer set 16 is configured as shown in the example of FIG. 3, mechanical connectors 82, 84 and/or the containers to which the connectors join may be disinfected by wiping a cloth containing a disinfectant over the surfaces of the mechanical connectors and/or containers to which the pathogen was applied.

In addition to or in lieu of disinfecting the one or more components of fluid delivery system 10 (201) after applying the pathogen (200) as described above, the one or more components of fluid delivery system 10 may be disinfected prior to applying the pathogen (200). For example, a disinfectant designed to kill and/or remove the pathogen can be applied to surfaces of the components where the pathogen is to be applied. Disinfecting the surfaces of the components where the pathogen is to be applied can clean and sterilize the components. This can help ensure that any pathogenic ingress subsequently identified in fluid delivery system 10 is attributable to the controlled application of the pathogen according to the technique of FIG. 5A and not external sources. When disinfected prior to applying the pathogen, the one or more components of fluid delivery system 10 can be disinfected, e.g., using the techniques described above for disinfecting the one or more components after application of the pathogen.

Independent of whether the one or more components of fluid delivery system 10 are disinfected, the components may be assembled (202) to place the components in fluid communication with one another. When the one or more components are disinfected prior to assembly (201), the components may first be allowed to dry for a period of time prior to assembly such as a period of greater than 10 seconds, greater than 30 seconds, or greater than approximately 1 minute. The components of fluid delivery system 10 can be assembled in accordance with fluid delivery system use instructions. To assemble fluid transfer set 16 (FIG. 1) in fluid delivery system 10, for example, an operator can mate a mechanical connector positioned at a proximal end 34 of the fluid transfer set with container 14. As the mechanical connector is mated with container 14, the connector may pierce a seal on the container, allowing fluid to flow from the container into the fluid transfer set. The operator may also mate a mechanical connector at distal end 36 of the fluid transfer set with fluid pressurizing unit 18 so as to place the fluid transfer set in fluid communication with the pressurizing unit.

With further reference to FIG. 5A, the example technique also includes drawing fluid from container 14 through fluid transfer set 16 and into fluid pressurizing unit 18 (203). Subsequent to applying the pathogen to the one or more components of fluid delivery system 10 (200) and disinfecting (201) and assembling (202) the components, fluid is drawn through the system to evaluate if the pathogen will enter the fluid during typical filling and injection operations. Fluid may be drawn from container 14 through fluid transfer set 16 and into fluid pressurizing unit 18 immediately after applying the pathogen or after the pathogen has been applied for a certain amount of time. For example, fluid may be drawn through fluid delivery system 10 after the pathogen has been applied and allowed to reside in or on the components of the system for a period of at least 1 hour such as, e.g., a period greater than or equal to 4 hours, a period greater than or equal to 8 hours, or a period greater than or equal to 10 hours. Of course, the fluid delivery components may first be disinfected (201), allowed to dry, and assembled after the pathogen is allowed to reside on the components for any of the foregoing periods of time.

The technique of FIG. 5A also includes extracting a sample of medical fluid from within fluid delivery system 10 (204). The fluid sample may be extracted by operating fluid pressurizing unit 18 to discharge pressurized medical fluid through discharge outlet 28. The sample may be collected at the discharge outlet, e.g., from discharge line 30. Additionally or alternatively, a fluid sample may be extracted by disconnecting detachably connected components in fluid delivery system 10 and extracting a sample of fluid from within the components. For example, fluid transfer set 16 may be detached from container 14 and/or fluid pressurizing unit 18 and a sample of fluid taken from within container 14, from within the fluid transfer set, and/or from within fluid pressurizing unit 18.

Independent of the specific technique used to extract a sample from fluid delivery system 10 (204), the sample is subsequently analyzed (206) to determine a concentration level of the pathogen applied to the fluid delivery system in the fluid sample. The determined pathogen level may be compared to a concentration level of the pathogen in the medical fluid within container 14 before the container was connected to fluid delivery system 10 and challenged with the pathogen. For example, a concentration level of the pathogen in the medical fluid within container 14 before the container was connected to fluid delivery system 10 and challenged with the pathogen may be zero. If the extracted sample is determined to also have a pathogen concentration level of zero, fluid delivery system 10 may be validated as successfully resisting the passage of microorganisms into fluid pathways. Different tolerance levels may be established depending on the requirements of a particular application.

Figure 5B:
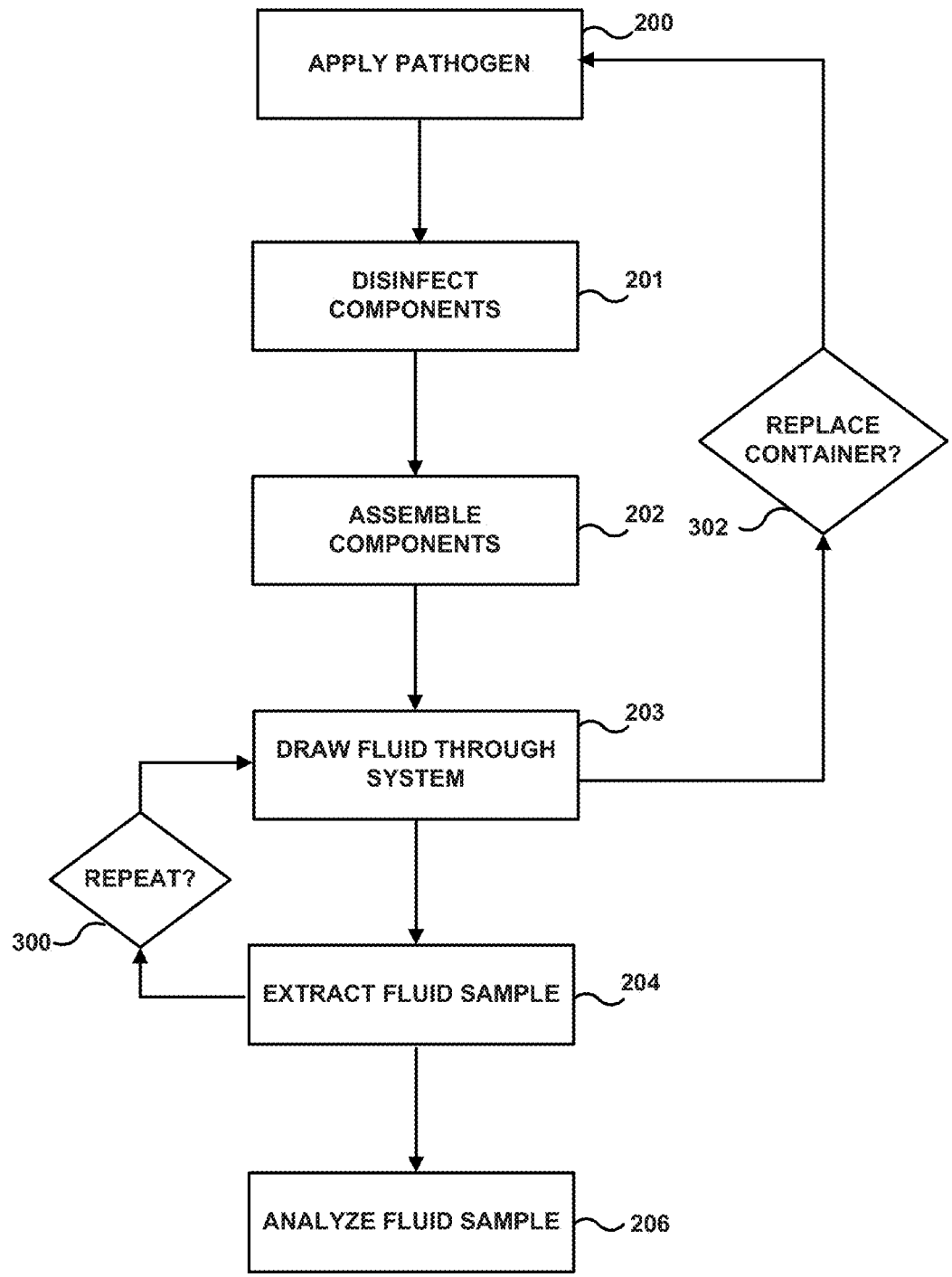

FIG. 5B is a flow diagram of an example implementation of the technique of FIG. 5A, where like process steps described above with respect to FIG. 5A are designated with like reference numerals. As shown in FIG. 5B, the example technique includes applying one or more pathogens (e.g., one or more bacteria and/or viruses) to the one or more components of fluid delivery system 10 (200), such as a portion of a component or portions of components that join together to form a connection. Subsequent to applying the pathogen to the one or more components of fluid delivery system 10 (200), the components may be disinfected (201) and assembled (202) to place the components in fluid communication with one another.

Once the pathogen challenged components are assembled, fluid is drawn through the system to evaluate if the pathogen will enter the fluid during typical filling and injection operations (203). Fluid can be drawn from container 14 through fluid transfer set 16 and into fluid pressurizing unit 18 by operating (e.g., activating) the fluid pressurizing unit. In the technique of FIG. 5B, fluid pressurizing unit 18 is operated multiple times (300) to discharge multiple portions of fluid from the fluid pressurizing unit 18 via discharge outlet 28. For example, fluid pressurizing unit 18 may be activated a first time to draw fluid from container 14 through fluid transfer set 16 and then discharge a first portion of pressurized fluid out through discharge outlet 28. After dispensing a suitable volume of fluid, fluid pressurizing unit 18 may cease operation so that no fluid is being dispensed from discharge outlet 28. Fluid pressurizing unit 18 may subsequently be activated a second time to draw additional fluid from container 14 through fluid transfer set 16 and discharge a second portion of pressurized fluid out through discharge outlet 28. After discharging a suitable volume of fluid, fluid pressurizing unit 18 may again cease operation so that no fluid is being dispensed from discharge outlet 28. The process of activating fluid pressurizing unit 18 and ceasing operation of the unit can be repeated any additional number of times, such as one, two, three, or more times, e.g., to convey a certain volume of fluid and/or generate a certain number of discharged fluid portions.

Operating fluid pressurizing unit 18 multiple times to generate multiple portions of fluid (300) may be useful to simulate real-world operation of fluid delivery system 10 when the system is used to inject multiple patients with fluid from container 14 during multiple sequential patient injection procedures. During each patent injection procedure, fluid pressurizing unit 18 is operated to draw fluid from container 14 and discharge the fluid under pressure into catheter 32 connected to a patient. After each patient injection procedure, fluid pressurizing unit 18 ceases operation and, in some examples, is replaced with a new, sterile fluid pressurizing unit. The fluid pressurizing unit can then be operated during a subsequent injection procedure to inject a new patient with pressurized medical fluid. The process can be repeated for additional patient injection procedures.

By operating fluid pressurizing unit 18 multiple times to discharge multiple portions of fluid (300) during validation testing, fluid delivery system 10 can be evaluated for resistance to pathogenic ingress during a normal course of operation. Fluid pressurizing unit 18 can be operated any desired number of times to generate any desired number of portions or volumes of fluid during the performance of the method of FIG. 5B. In some examples, fluid pressurizing unit 18 is operated at least twice (e.g., three, four, or more times) to provide at least two portions of fluid (e.g., three, four, or more portions of fluid) that are discharged from the fluid pressurizing unit during operation. Fluid pressurizing unit 18 may cease operation for a given period of time between each cycle in which the unit is operated to discharge fluid. For example, the fluid pressurizing unit 18 may remain inactive for a period of at least 5 minutes between each cycle of operation, such as a period of at least 20 minutes, a period of at least one hour, a period of at least 2 hours, a period ranging from 5 minutes to 5 hours, or a period ranging from 10 minutes to 2 hours. As described in greater detail below, a fluid sample can be extracted from one more of the portions of fluid discharged from fluid pressurizing unit 18 for subsequent analysis (204).

The volume of fluid discharged from fluid pressurizing unit 18 during the performance of the technique of FIG. 5B can vary, e.g., depending on the capacity of container 14, the discharge rate of the fluid pressurizing unit, and the amount of time the fluid pressurizing unit is operated during each cycle. Moreover, when attempting to simulate real-world operation of fluid delivery system 10, the fluid delivery system can, in different operating environments, be operated in a low volume throughput scenario in which only a few patients would be injected during a day of operation or a high volume throughput scenario in which many patients would be injected during a day of operation.

In a comparatively low volume throughput environment, fluid delivery system 10 may be connected to a single container 14 (e.g., contrast, saline) or single set of containers (e.g., a container of contrast and a container of saline) that are used throughout a single day without replacement. Accordingly, to simulate comparatively low volume operation, fluid pressurizing unit 18 may be operated so that each portion of fluid discharged from the fluid pressurizing unit is drawn from the same container or set of containers, e.g., without replacing a container between operating cycles of the fluid pressurizing unit. In such an application, each sample of fluid extracted from fluid delivery system 10 (204) and analyzed for the pathogen (206) may originate from the same container or set of containers. In some cases, each sample of fluid may be obtained from a discharged portion of fluid without disassembling fluid system 10 (e.g., disconnecting container 14, fluid transfer set 16, and/or fluid pressurizing unit 18), which may otherwise introduce contamination into the system.

As one example of a low volume throughput simulation, specifically when fluid transfer set 16 is configured as shown in the example of FIG. 3, connector 82 may be attached to a container of contrast sized to provide multiple doses of fluid to multiple different patients (e.g., 500 milliliters) and connector 84 may be attached to a container of saline sized to provide multiple doses of fluid to multiple different patients (e.g., 500 milliliters). Fluid pressurizing unit 18 can then be periodically operated to dispense a portion of fluid that is drawn from the container of contrast and/or the container of saline. For example, to simulate a patient dose, fluid pressurizing unit 18 may be operated to dispense 100 milliliters of contrast followed by 30 milliliters of saline, thereby dispensing a first portion of fluid that is 130 milliliters. Fluid pressurizing unit 18 may be operated to subsequently dispense additional portions of fluid that are each composed of 100 milliliters of contrast followed by 30 milliliters of saline. For example, fluid pressurizing unit 18 may be operated to dispense a first portion of fluid upon initial assembly of fluid delivery system 10, a second portion of fluid four hours after assembly, a third portion ten hours after assembly, and a fourth portion twelve and a half hours after assembly. The container of contrast and container of saline in such an example would have a capacity sufficient to allow all four portions of fluid to be drawn from the same set of containers.

In contrast to a low volume throughput environment, in a comparatively high volume throughput environment, the container 14 (e.g., contrast, saline) or a set of containers (e.g., a container of contrast and a container of saline) connected to fluid delivery system 10 may be replaced throughout a day of operation as the contents of the containers are exhausted. Accordingly, to simulate comparatively high volume operation, fluid pressurizing unit 18 may be operated a sufficient number of times to empty the container or set of containers. Upon emptying the containers, the container or set of containers to which fluid pressurizing unit 18 is fluidly connected may be replaced with a replacement container or set of containers filled with medical fluid (302). After replacement, fluid pressurizing unit 18 may again be operated to dispense portions of fluid from the replacement containers.

As one example of a high volume throughput simulation, specifically when fluid transfer set 16 is configured as shown in the example of FIG. 3, connector 82 may be attached to a container of contrast sized to provide a dose of fluid to multiple different patients (e.g., 200 milliliters) and connector 84 may be attached to a container of saline sized to provide a dose of fluid to multiple different patients (e.g., 500 milliliters). Fluid pressurizing unit 18 can then be periodically operated to dispense a portion of fluid that is drawn from the container of contrast and/or the container of saline. For example, to simulate a patient dose, fluid pressurizing unit 18 may be operated to dispense 100 milliliters of contrast followed by 30 milliliters of saline, thereby dispensing a first portion of fluid that is 130 milliliters. Fluid pressurizing unit 18 may be operated additional times at a frequency sufficient to consume multiple containers of contrast and/or multiple containers of saline over a given period of time. For example, fluid pressurizing unit 18 may be operated at a frequency sufficient to consume twenty containers of contrast and four containers of saline over a twelve and a half hour period by dispensing discrete 130 milliliter portions of contrast and saline. The containers of contrast and saline may be replaced with full replacement containers as the in-service containers connected to fluid delivery system 10 become exhausted. In such an application, different samples of fluid extracted from fluid delivery system 10 (204) and analyzed for the pathogen (206) may originate from different containers or different sets of containers. Such an application may be useful to evaluate the tendency of the pathogen to invade fluid system 10 during the course of high volume operation when medical fluid containers are being replaced multiple times per day.

Independent of whether fluid delivery system 10 is operated to simulate low volume throughput, a high volume throughput, or both low and high volume throughputs, the technique of FIG. 5B includes applying the pathogen to one or more components in fluid delivery system 10 (200). For example, when fluid transfer set 16 is configured as shown in the example of FIG. 3, the pathogen may be applied to connector 82 (e.g., a connection between a container such as container 14 and connector 82), a proximal end 66 of the first length of tubing 64 and connector 82 (e.g., a connection between the components), at connector 84 (e.g., a connection between a container and connector 84), and/or at a connection between fluid pressurizing unit inlet connector 86 and pump 62. After applying the pathogen to the components (200), the components may be disinfected (201) and assembled (202), as described with respect to FIG. 5A.

In instances where a fluid container or set of fluid containers is replaced during performance of the method of FIG. 5B (302), the pathogen may or may not be reapplied to some or all of the connection locations where the pathogen was applied during initial assembly of fluid delivery system 10. Reapplying the pathogen may be useful to evaluate the tendency of the pathogen to invade fluid system 10 during the course of high volume operation when medical fluid containers are being replaced multiple times per day. When the pathogen is reapplied, the components may again be disinfected (201) and then reassembled (202).

After or while operating fluid pressurizing unit 18 multiple times over a given period to draw fluid through fluid delivery system 10 and dispense multiple portions of fluid from the unit (203), a plurality of fluid samples of fluid are extracted for analysis (204). Each sample of fluid may be from a different portion of fluid dispensed during a different cycle of operation of fluid pressurizing unit 18. In one example, a sample of fluid is obtained from each portion of fluid discharged from fluid pressurizing unit 18. In another example, a sample of fluid is obtained from some but not all portions of fluid discharged from fluid pressurizing unit 18. For example, an operator may extract a sample from a first portion of fluid dispensed from fluid pressurizing unit 18 upon initial assembly of fluid delivery system 10 and/or a sample from a last portion of fluid dispensed from the fluid pressurizing unit during a final operation. An operator may extract additional or different samples. For instance, in addition to extracting a sample from a first portion of fluid and a sample from a last portion of fluid, the operator may extract one or more (e.g., two, three, or more) additional samples from portions of fluid dispensed between the first portion of fluid and the last portion of fluid.

The technique of FIG. 5B also includes analyzing the plurality of samples (206) to determine a concentration level of the pathogen applied to the fluid delivery system in the plurality of fluid samples. In some examples, each of the plurality of samples obtained from the multiple portions of fluid are combined together to form a pooled sample. In such applications, the pooled sample may be analyzed to determine a concentration level of the pathogen in the pooled sample. In other examples, each of the plurality of samples is separately analyzed to determine a concentration level of the pathogen in each respective sample. In either case, if a sample is determined to have a low concentration level (e.g., zero) for the pathogen or combination of pathogens originally applied to fluid delivery system 10, the fluid delivery system may be validated as successfully resisting the passage of microorganisms into fluid pathways.

In some examples, the technique of FIG. 5B is repeated under both high volume throughput conditions and low volume throughput conditions to validate fluid delivery system 10, or a component thereof. For example, the technique may be performed once under high throughput conditions in which multiple containers of contrast and/or saline are consumed to generate samples of discharged fluid that originated from different containers or sets of containers. The samples obtained during high throughput testing can be pooled together and analyzed to determine a concentration level of the pathogen in the pooled sample. In addition, the technique may be performed again under low throughput conditions. In low throughput conditions, only a single container or set of containers of contrast and/or saline may be consumed to generate samples of discharged fluid that all originated from the same container or set of containers. The samples obtained during low throughput testing can also be pooled together and analyzed to determine a concentration level of the pathogen in the pooled sample. In some applications, fluid delivery system 10 may be validated as successfully resisting the passage of microorganisms into fluid pathways if both the pooled sample from high throughput testing and the pooled sample from low throughput testing are determined to have a sufficiently low concentration level (e.g., zero) of the pathogen.

Figure 6:
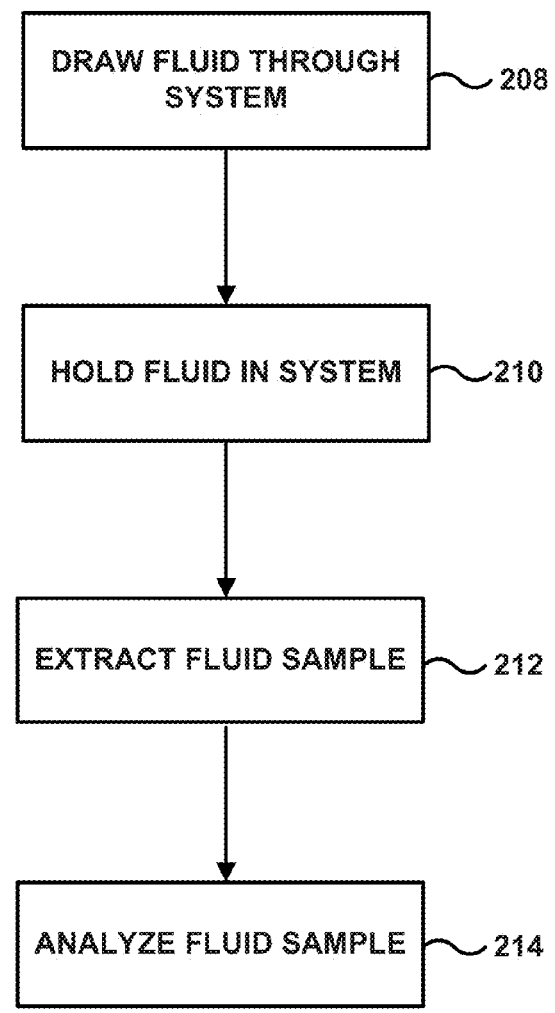

FIG. 6 is a flow diagram illustrating another example technique that may be used to validate the integrity and sterility of a medical fluid delivery system. The components of the medical fluid delivery system may be assembled together (e.g., so that a fluid transfer set is in fluid communication with both a container of medical fluid and a fluid pressurizing unit). Once assembled, the example technique includes drawing fluid from container 14 through fluid transfer set 16 and into fluid pressurizing unit 18 so as to fill fluid holding areas in fluid delivery system 10 with medical fluid (208). Although fluid delivery system 10 can be filled with any medical fluid as described herein, in some examples, the medical fluid is contrast media. By filling fluid delivery system 10 with contrast media, a user may determine the ability of the components of fluid delivery system 10 to resist chemical degradation, including multi-use components that may be used during the course of multiple patient injections.

Subsequent to filling fluid transfer set 16 and fluid pressurizing unit 18 with medical fluid, the medical fluid is held in the fluid transfer set and fluid pressurizing unit for a period of time (210). The components of fluid delivery system 10 may be held full of fluid for a period of time so that the fluid contacts interior surfaces of the components that would normally be fluid-wet during filling and/or discharge of powered fluid injector 12. In some examples, the fluid is static (e.g., not moving) within fluid delivery system 10 as the components of the system are held full of fluid. In other examples, the fluid may be moving through fluid delivery system 10 during the period of time in which the components are held full of fluid.

The components of fluid delivery system 10 can be held full of fluid for any period of time suitable for evaluating the ability of the components to resist chemical degradation (210). In applications where a multi-use component is intended to remain in service during the course of multiple fluid injections, the component may be exposed to fluid continuously or intermittently for an extended period of time such as an entire shift or entire day. Accordingly, in some examples, the components of fluid delivery system 10 may be held full of fluid for a period of time greater than or equal to 1 hour such as, e.g., a period of time greater than or equal to 2 hours, a period of time greater than or equal to 4 hours, or a period of time greater than or equal to 8 hours. For instance, the components of fluid delivery system 10 may be held full of fluid for a period of time ranging from approximately 1 hour to approximately 48 hours such as, e.g., from approximately 4 hours to approximately 24 hours, or approximately 8 hours to approximately 16 hours.

After holding the components of fluid delivery system 10 (e.g., fluid transfer set 16 and fluid pressurizing unit 18) full of medical fluid, a sample of the medical fluid can be extracted for analysis (212). The fluid sample may be extracted by operating fluid pressurizing unit 18 to discharge pressurized medical fluid through discharge outlet 28. The sample may be collected at the discharge outlet. Additionally or alternatively, a fluid sample may be extracted by disconnecting detachably connected components in fluid delivery system 10 and extracting a sample of fluid from within the components. For example, fluid transfer set 16 may be detached from container 14 and/or fluid pressurizing unit 18 and a sample of fluid taken from within container 14, from within the fluid transfer set, and/or from within fluid pressurizing unit 18.

The extracted sample is analyzed to determine if any components of the fluid delivery system have chemically degraded with exposure to the medical fluid (214). The fluid may be analyzed to determine if a material(s) used to fabricate components of fluid delivery system 10 (e.g., a material used to fabricate fluid transfer set 16 and/or fluid pressurizing unit 18) have entered the medical fluid held within the components. In one example, the fluid is analyzed to determine if there are any particles in the fluid greater than a certain size such as, e.g., greater than 10 micrometers, greater than 100 micrometers, or greater than 1 millimeter. Such particles may be pieces of a component of fluid delivery system 10 that have detached from the component. If the extracted sample is determined to not have particles greater than a certain size or not have a certain number of particles greater than the certain size, fluid delivery system 10 may be validated as being chemically compatible and maintaining chemical integrity with the medical fluid (e.g., the class of medical fluids).

In addition to or in lieu of analyzing the extracted sample for particles, the extracted sample may be analyzed to determine if a chemical present in the material(s) used to fabricate components of fluid delivery system 10 (e.g., a material used to fabricate fluid transfer set 16 and/or fluid pressurizing unit 18) has leached into the medical fluid held within the components. As examples, the extracted fluid sample may be analyzed to determine if one or more of the following chemical compounds are present in the fluid: cyclohexanone, 2-ethyl-1-hexanol, di(2-ethylhexyl)phthalate (DEHP), epoxidized soybean oil, tris(nonylphenyl)phosphate (TNPP), stearic acid, zinc or other heavy metals. The extracted sample may be analyzed using gas chromatography, high-performance liquid chromatography, inductively coupled plasma mass spectrometry (ICP-MS), or any other suitable techniques. A determined concentration level of the chemical compound(s) may be compared to a concentration level in the medical fluid within container 14 before the container was connected to fluid delivery system 10 and exposed to the components in the system. For example, a concentration level of the chemical compound(s) in the medical fluid within container 14 before the container was connected to fluid delivery system 10 and drawn through the system may be zero. If the extracted sample is determined to also have a concentration level of zero for the chemical compound(s), fluid delivery system 10 may be validated as being chemically compatible and not leaching chemical compound(s) into the medical fluid. Different tolerance levels may be established depending on the requirements of a particular application.

Figure 7A:
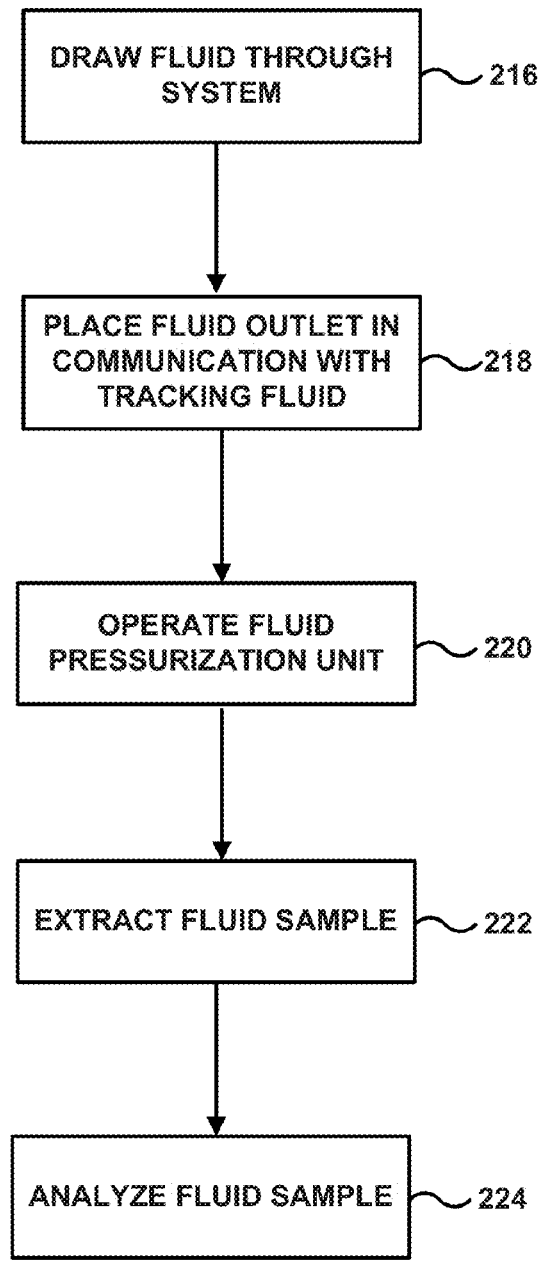

FIG. 7A is a flow diagram illustrating another example technique that may be used to validate the integrity and sterility of a medical fluid delivery system. The technique may be used to confirm that cross-contamination of fluids between patients will not occur when using fluid delivery system 10 by having fluid from a patient-specific tube (e.g., downstream of fluid pressurizing unit 18) mix with fluid in a multi-use tube (e.g., upstream of fluid pressurizing unit 18). The components of the medical fluid delivery system may be assembled together (e.g., so that a fluid transfer set is in fluid communication with both a container of medical fluid and a fluid pressurizing unit). Once assembled, the example technique includes drawing fluid from container 14 through fluid transfer set 16 and into fluid pressurizing unit 18 so as to fill fluid holding areas in fluid delivery system 10 with medical fluid (216). By drawing medical fluid from container 14 through fluid transfer set 16 and into fluid pressurizing unit 18, the fluid holding regions of fluid delivery system 10 upstream of fluid pressurizing unit 18 may be filled with medical fluid.

In addition, in the technique of FIG. 7A, discharge outlet 28 of fluid delivery system 10 is placed in fluid communication with a fluid reservoir containing a tracking fluid (218). The fluid reservoir may be a bottle, bag, pouch, syringe, or tube filled with fluid, or any other suitable reservoir. The tracking fluid may contain a tracking agent not present in the medical fluid in container 14. The tracking agent may be tracked to determine if fluid downstream of discharge outlet 28 migrates into fluid pressurizing unit 18 and/or upstream of fluid pressurizing unit 18. For example, the tracking agent may simulate the movement of blood borne pathogens, were discharge outlet 28 in fluid communication with a catheter inserted into a patient. Example tracking agents may include, but are not limited to, bacteria, viruses, dyes, radioactive isotopes, and electro-magnetic markers.

To simulate cross-contamination conditions, the fluid reservoir containing the tracking agent is blocked so that fluid pressurizing unit 18 cannot draw medical fluid from container 14 and inject the fluid into the fluid reservoir containing the tracking agent. Configuring the fluid reservoir containing the tracking agent as a closed reservoir may simulate conditions in which a patient's catheter 32 is blocked and fluid pressurizing unit 18 is attempting to inject fluid into a blocked or partially occluded catheter. Were the fluid reservoir containing the tracking agent not closed, fluid pressurizing unit 18 could draw fluid from container 14 and inject the fluid into the reservoir, preventing the tracking agent from migrating upstream in fluid delivery system 10. By contrast, when fluid pressurizing unit 18 discharges medical fluid through discharge outlet 28 against a closed reservoir of tracking fluid, a generally static interface may be created where discharged medical fluid meets tracking fluid, potentially resulting in mixing and upstream migration of the tracking fluid into the upstream medical fluid.

Accordingly, after placing discharge outlet 28 of fluid delivery system 10 in fluid communication with a fluid reservoir containing a tracking fluid (218), fluid pressurizing unit 18 is operated to try and discharge pressurized medical fluid into the tracking fluid (220). For example, when fluid pressurizing unit is a pump, the pump may operate continuously for a period of time even though the pump may not necessarily be conveying fluid because the fluid path downstream of the pump is blocked or restricted. Fluid pressurizing unit 18 may operate for any suitable period such as, e.g., greater than 1 minute, greater than 15 minutes, greater than 30 minutes, or greater than 1 hour.

After operating fluid pressurizing unit 18 for a period of time (220), a sample of medical fluid is extracted from fluid delivery system 10 for analysis (222). The fluid sample may be extracted by disconnecting detachably connected components in fluid delivery system 10 and extracting a sample of fluid from within the components. For example, fluid transfer set 16 may be detached from container 14 and/or fluid pressurizing unit 18 and a sample of fluid taken from within container 14, from within the fluid transfer set, and/or from within fluid pressurizing unit 18.

The extracted sample is analyzed to determine a concentration level of the tracking agent in the sample of medical fluid (224). The determined concentration level may be compared to a concentration level of the tracking agent in the medical fluid within container 14 before the container was connected to fluid delivery system 10. For example, a concentration level of the tracking agent in the medical fluid within container 14 and/or transfer set 16 before the container was connected to fluid delivery system 10 may be zero. If the extracted sample is determined to also have a concentration level of zero, fluid delivery system 10 may be validated as successfully preventing cross-contamination of fluid between a patient-specific fluid line and a multi-use fluid line. Different tolerance levels may also be established depending on the requirements of a particular application.

Figure 7B:
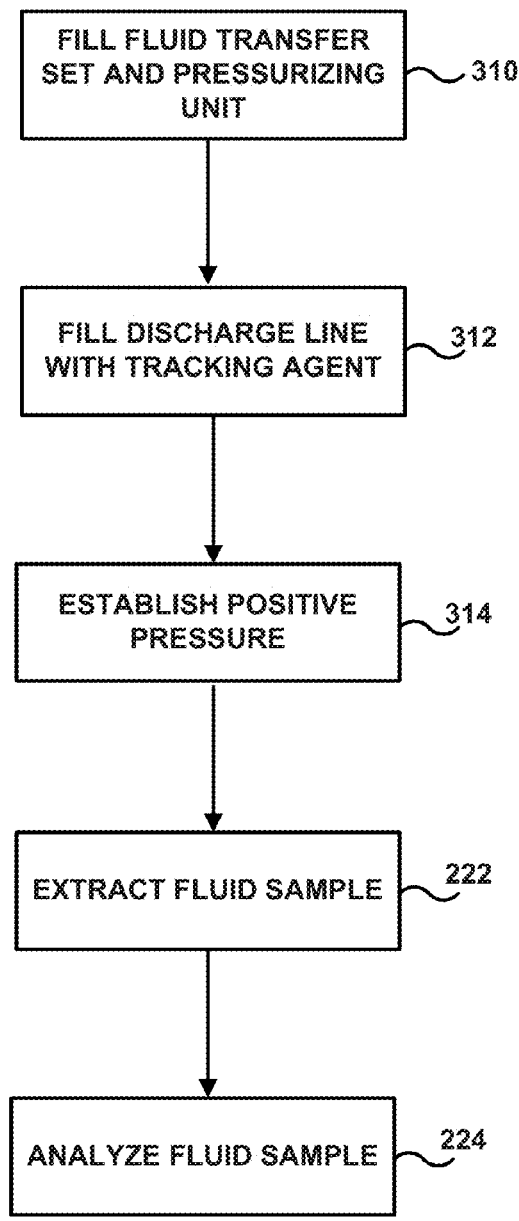

FIG. 7B is a flow diagram illustrating another example technique that may be used to confirm that cross-contamination of fluids between patients will not occur when using fluid delivery system 10, where like process steps described above with respect to FIG. 7A are designated with like reference numerals. In the technique of FIG. 7B, the components of the medical fluid delivery system may be assembled together (e.g., so that fluid transfer set 16 is in fluid communication with both container 14 and fluid pressurizing unit 18). Once assembled, the example technique includes filling fluid transfer set 16 and fluid pressurizing unit 18 with medical fluid (310). The components can be filled with fluid by activating fluid pressurizing unit 18 to draw fluid from container 14 through fluid transfer set 16 and into the fluid pressurizing unit. This can prime fluid pressurizing unit 18 and/or fill fluid holding areas in fluid delivery system 10 with medical fluid, thus providing filled fluid pathway(s) to evaluate whether a tracking agent will travel through the pathways, potentially indicating a risk of cross-contamination. In some examples, fluid transfer set 16 and fluid pressurizing unit 18 are filled with a comparatively low viscosity medical fluid, such as saline, which may be more prone to permit flow of a tracking agent than a comparatively higher viscosity fluid, such as contrast.

In addition, in the technique of FIG. 7B, a discharge line (e.g., discharge line 30 in FIG. 3) connected to discharge outlet 28 of fluid pressurizing unit 18 is filled with a tracking agent (312). The tracking agent may be a tracking fluid containing a tracking agent and, in different examples as described above with respect to FIG. 7A, can be a bacteria, virus, dye, radioactive isotope, and/or electro-magnetic marker. The discharge line may be filled by introducing the tracking agent through a distal outlet of the discharge line (e.g., opposite fluid pressurizing unit 18) and allowing the tracking agent to flow down the discharge line toward the fluid pressurizing unit. Upon initially filling the discharge line with tracking agent, the tracking agent may be positioned between discharge outlet 28 of fluid pressurizing unit 18 and a distal end of discharge line 30 extending away from discharge outlet 28.

When filling a discharge line with tracking agent (312), the tracking agent can be introduced into the discharge line until it is positioned any suitable distance from fluid pressurizing unit 18. In general, the distance between the tracking agent in the discharge line and the fluid pressurizing unit can be controlled by controlling the amount of medical fluid in the discharge line before introduction of the tracking agent. For example, if fluid pressurizing unit 18 was primed with medical fluid and the discharge line was filled with a column of medical fluid extending approximately 10 centimeters away from the fluid pressurizing unit, the tracking agent may initially be positioned approximately 10 centimeters away from the fluid pressurizing unit, when introduced into the discharge line. In such an example, the column medical fluid that does not contain tracking agent may function to initially separate the tracking agent from the fluid pressurizing unit.

Figure 8A:
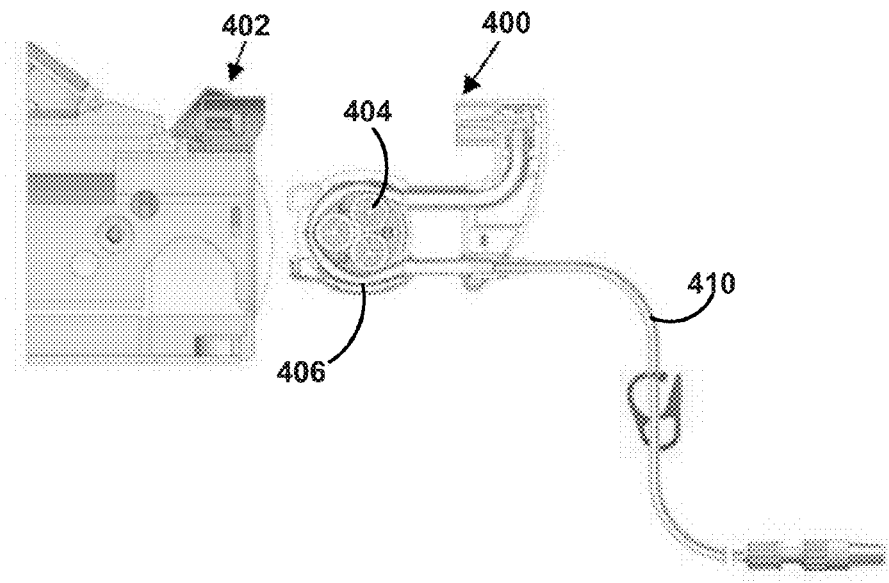
FIGS. 8A and 8B are perspective drawings of an example peristaltic pump that has a fluid seal and may be used as a fluid pressurizing unit.
Figure 8B:
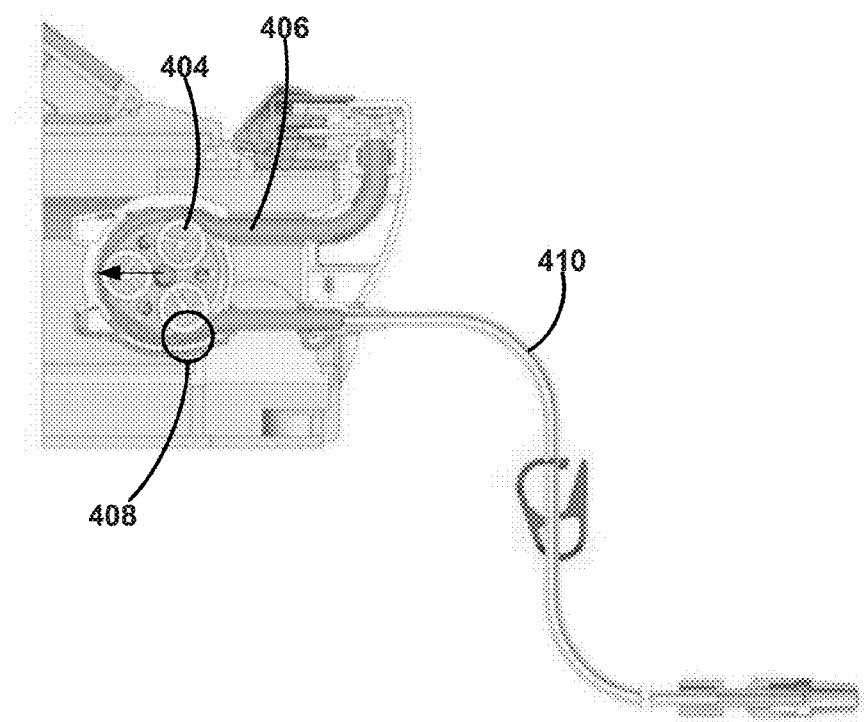

In some examples, fluid pressurizing unit 18 provides a fluid seal adjacent discharge outlet 28 and the discharge line is filled with tracking agent until the tracking agent is positioned adjacent the fluid seal. FIGS. 8A and 8B are perspective drawings of an example peristaltic pump 400 that has a fluid seal and may be used as fluid pressurizing unit 18. FIG. 8A illustrates peristaltic pump 400 outside of and insertable into a pump housing 402, while FIG. 8B illustrates the peristaltic pump inserted into the pump housing.

As shown in the examples of FIGS. 8A and 8B, peristaltic pump 400 has a plurality of rollers 404 that are configured to squeeze (e.g., compress) a compressible tube 406. For example, when peristaltic pump 400 is inserted into pump housing 402 as illustrated in FIG. 8B, rollers 404 may push radially outwards to compress compressible tube 406 between each of the rollers and an opposite wall surface of the pump. Rotation of the plurality of rollers 404 pressurizes and moves medical fluid through the tube. In addition, locations where each of the plurality of rollers 404 impinges upon the tube may define a fluid seal, such as fluid seal 408. Fluid seal 408 can be a location where the cross-sectional flow area of compressible tube 406 is minimized compared to other areas of the tube and/or completely closed due to the compressive action of the rollers.

Figure 9:
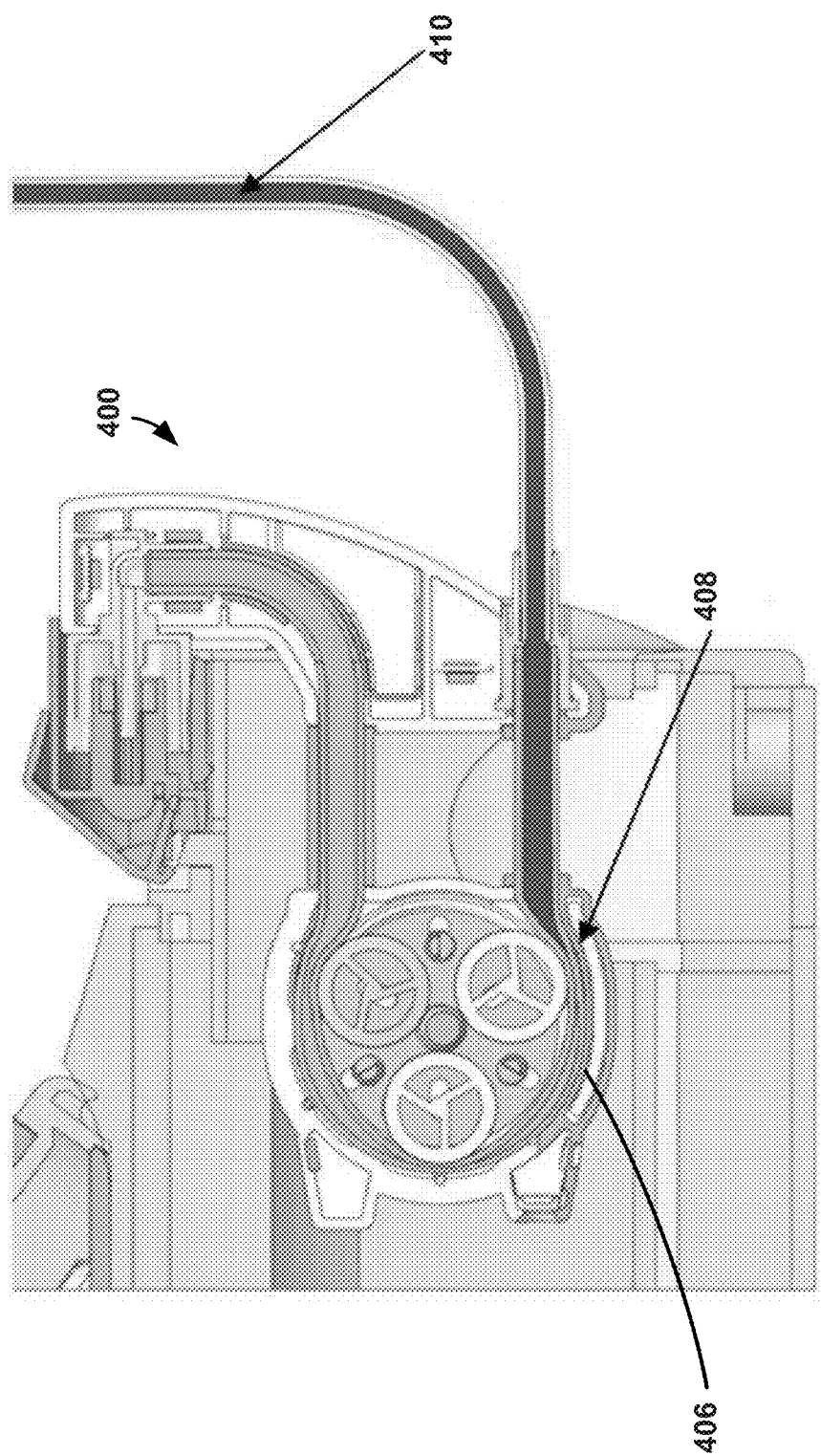
FIG. 9 is a perspective drawing of the peristaltic pump of FIGS. 8A and 8B illustrating a discharge line filled with a tracking agent.

Filling a fluid pressurizing unit, such as peristaltic pump 400, with tracking agent so the tracking agent is positioned adjacent to fluid seal 408 may be useful to simulate a worst case cross-contamination scenario in which a simulated contaminant (tracking agent) is best positioned to cross from a single-patient discharge line and/or single-patient fluid pressurizing unit back into a multi-patient fluid transfer set. FIG. 9 is a perspective drawing of peristaltic pump 400 illustrating a discharge line 410 filled with tracking agent. The discharge line is filled with tracking agent so the tracking agent is positioned adjacent to fluid seal 408. In particular, in the illustrated example, the tracking agent impinges on fluid seal 408. When so configured, tracking agent may extend into a region of compressible tube 406 where the cross-sectional flow area of the compressible tube is minimized compared to other areas of the tube and/or completely closed due to the compressive action of the rollers pressing on the tube.

With further reference to FIG. 7B, the example technique also includes establishing a positive pressure that biases the tracking agent in the discharge line toward the fluid pressurizing unit (314). To simulate cross-contamination conditions, a pressure may be applied to the tracking agent in the discharge line that attempts to force the tracking agent back through fluid pressurizing unit 18 and into fluid transfer set 16. The ability of fluid pressurizing unit 18 to resist migration of tracking agent back into fluid transfer set 16 may indicate cross-contamination resistance capabilities of the system.

Any suitable technique can be used to establish a positive pressure that acts on the tracking agent in the discharge line. In one example, a positive pressure source (e.g., a pressurized liquid or gas) is connected to a distal end of the discharge line, thereby establishing a positive pressure that biases fluid in the discharge line toward fluid pressurizing unit 18. In another example, the discharge line is oriented vertically with a distal end of the line open to ambient atmosphere. In such an example, a fluid head pressure provided by the weight of the fluid in the discharge line and gravity acting on the fluid can provide positive pressure that biases the tracking agent toward fluid pressurizing unit 18. For example, peristaltic pump 400 is illustrated in FIG. 9 with discharge line 410 extending vertically upward with respect to ground to provide a positive pressure that biases the tracking agent toward the pump.

Independent of the specific technique used to establish a positive pressure, any suitable magnitude of pressure may act on the tracking agent to bias the tracking agent back toward the fluid pressurizing unit. In some examples, the tracking agent is biased with a positive pressure greater than 0.05 pounds per square inch gauge (psig), such as greater than 0.1 psig, greater than 0.25 psig, greater than 0.5 psig, or greater than 1 psig. For example, the positive pressure acting on the tracking agent at the proximal end of the discharge tube immediately adjacent fluid pressurizing unit 18 may range from 0.05 psig to 5 psig, such as from 0.1 psig to 2 psig, or from 0.25 psig to 1 psig. In one example, the pressure is greater than or equal to an average peripheral venous pressure of a human, which is typically reported as approximately 0.3 pounds per square inch. Fluid pressurizing unit 18 will typically not be operating while the positive pressure is acting on the tracking agent.

The technique of FIG. 7B also includes extracting a sample of medical fluid from fluid delivery system 10 (222) and analyzing the sample to determine a concentration level of the tracking agent in the sample (224), as discussed above with respect to FIG. 7A. Medical fluid may be extracted from fluid delivery system 10 (222) after the established positive pressure (314) is allowed to act on the tracking agent for a given period of time. In general, the longer the tracking agent is held under pressure and biased against fluid pressurizing unit 18, the more likely the tracking agent is to bypass the pressurizing unit and enter medical fluid in fluid transfer set 16. In different examples, the tracking agent is held under positive pressure for a period of at least 5 minutes, such as at least 15 minutes, at least 30 minutes, at least 1 hour, at least 8 hours, or at least 1 day. For example, the tracking agent may be held with a positive pressure biasing the agent toward fluid pressurizing unit 18 for a period ranging from 5 minutes to 4 hours, such as a period ranging from 30 minutes to 2 hours.

While the example techniques of FIGS. 5A, 5B, 6, 7A, and 7B have been described as discrete techniques for validating the integrity and sterility of a medical fluid delivery system, it should be appreciated that any two of the techniques or all three of the techniques may be performed on a single fluid delivery system to validate different aspects of the system.

The following examples may provide additional details about validation techniques and validated components in accordance with this disclosure.

EXAMPLES

Example 1

Chemical Compatibility

A chemical compatibility study was performed to verify the chemical compatibility of the materials composing a Bracco transfer set [part no. 100115] similar to that shown in FIG. 2 with Isovue-370 contrast media as well as to check for the presence of sub-visible and visible particulates and potential leachable compounds in Isovue-370, which was subjected to contact with the transfer set during simulated use in accordance with the validation testing. The Bracco transfer set was configured as a disposable component intended to be used to fill injector syringes, such as injector syringes of the Bracco Empower CTA® and Medrad Stellant® injectors, with Isovue-370 contrast media from multi-dose, multi-patient containers.

To perform the chemical compatibility testing, a container closure of a 500 mL bottle of Isovue-370 was pierced with the Bracco transfer set and an injector was used to draw samples from the bottle through the transfer set into sterile, single use only injector syringe. Using a new syringe each time, 100 mL samples were dispensed at 0, 4, 10 and 14 hours by connecting the syringe to a tube and performing an injection of 100 mL into a chemically clean container. Each sample was subsequently analyzed along with a sample of the remaining contrast in the bottle at the end of the 14 hour testing protocol.

Each sample was evaluated to determine if any sub-visible or visible particles of material were released into the fluid. In addition, each sample was evaluated to determine if the following potentially leachable compounds leached into the fluid: di(2-ethylhexyl)phthalate (DEHP) and Octadecyl 3,5-Di-(tert)-butyl-4-hydroxyhydrocinnamate (Irganox 1076). The results of the particle analysis are provided in Table 1 below and the results of the leachable compounds analysis is provided in Table 2 below.

TABLE 1

| | Injector | | | | | |
|---|---|---|---|---|---|---|
| | Empower CTA ® | | | Medrad Stellant ® | | |
| Particles | Visible | >10μ | >25μ | Visible | >10μ | >25μ |
| Spec. | None | <5 particles per ml | <3 particles per ml | None | <25 particles per ml | <3 particles per ml |
| Time point | | | | | | |
| 0 hours | None | 10.13 | 0.27 | None | 6.53 | 0.40 |
| 4 hours | None | 8.27 | 0.93 | None | 3.60 | 1.07 |
| 10 hours | None | 13.33 | 0.53 | None | 12.40 | 0.53 |
| 14 hours | None | 16.80 | 0.40 | None | 2.80 | 0.40 |
| Remaining Contents of the Bottle at 14 Hrs. | None | 9.33 | 0.13 | None | 15.47 | 1.73 |

TABLE 2

| | Injector | | | | | |
|---|---|---|---|---|---|---|
| | Empower CTA ® | | Medrad Stellant ® | | Controls | |
| Time point | DEHP (μg/mL) | Irganox 1076 (μg/mL) | DEHP (μg/mL) | Irganox 1076 (μg/mL) | DEHP (μg/mL) | Irganox 1076 (μg/mL) |
| 0 hours | <1.0 | <2.5 | <1.0 | <2.5 | <1.0 | <2.5 |
| 4 hours | <1.0 | <2.5 | <1.0 | <2.5 | <1.0 | <2.5 |
| 14 hours | <1.0 | <2.5 | <1.0 | <2.5 | <1.0 | <2.5 |
| Remaining Contents of the Bottle at 14 Hrs. | <1.0 | <2.5 | <1.0 | <2.5 | <1.0 | <2.5 |

The results demonstrated that the chemical integrity of the Bracco transfer set was maintained when Isovue 370 was transferred via the transfer set to empty sterile, single use only syringes on automated power injectors. Chemical integrity was maintained throughout an extended hold period for the bottle of Isovue once the container closure was penetrated. Confirmation of chemical integrity included demonstration that the fluid samples exhibited sub-visible and visible particles within tolerance limits. Confirmation of chemical integrity also included a demonstration that the fluid samples lacked leachable compounds at levels of potential toxicological concern.

Example 2

Microbial Ingress Resistance

A microbial ingress resistance study was performed to verify the ability of a Bracco transfer set [part no. 100115]

similar to that shown in FIG. 2 and a multi-dose, multi-patient Isovue contrast media container to resist microbial ingress into fluid pathways under simulated operating conditions. The Bracco transfer set was configured as a disposable component intended to be used to fill injector syringes, such as injector syringes of the Bracco Empower CTA® and Medrad Stellant® injectors, with Isovue contrast media from the multi-dose, multi-patient containers.

To perform the testing, the injection systems were set up and operated using disposables that were surface contaminated (e.g., challenged) at specified locations (e.g., contact points) with a high concentration of viable microorganisms (10 µl of a ≥1,000 colony forming units per milliliter [CFU/mL]) and allowed to dry (<90 minutes). In particular, the disposables were challenged by applying a high concentration microorganism to each of the following contact points: a center of a septum of the multi-dose, multi-patient Isovue container; a side surface of a spike guard of the transfer set, around the base of the bottle spike; a Luer connection of the transfer set; and an exterior base of syringe tip. Using new, sterile disposables each time, individual tests were performed using each of the following bacteria: *Staphylococcus aureus, Staphylococcus epidermidis, Pseudomanas aeruginosa*, and *Klebsiella pneumonia*.

After allowing the bacteria to dry, the challenged contact points of the transfer set and the Isovue container septa were decontaminated with an alcohol wipe. The injectors were then set up and operated in accordance with the operator's manual for each injector system. Aliquots of the fluid that would normally be injected into a patient were collected from a distal end of a discharge line (e.g., patient line) attached to the injector syringe. Injection samples were dispensed at 0, 4, 10 and 14 hours after connection and assayed for sterility. In addition, a sample of the remaining contrast in the bottle at the end of the 14 hour testing protocol was collected and evaluated for sterility.

The results of the sterility testing are provided in Tables 3 and 4 below.

TABLE 3

| Challenge Site | *Staphylococcus epidermidis* | | *Klebsiella pneumoniae* | |
|---|---|---|---|---|
| Site Description | # Tests | Results | # Tests | Results |
| Center of septum of the bottle cap | 4 replicates of each set: T = 0 hr. T = 4 hr. T = 10 hr. T = 14 hr. Bottle For a total of 20 samples | No Growth in 20/20 samples | 4 replicates of each set: T = 0 hr. T = 4 hr. T = 10 hr. T = 14 hr. Bottle For a total of 20 samples | No Growth for 20/20 samples |
| Side surface of the spike guard of the transfer set, around the base of the bottle spike | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 20 samples | No Growth for 20/20 samples |
| The Luer connection of the transfer set | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 20 samples | No Growth for 20/20 samples |
| The exterior base of the syringe tip | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 19 samples | No Growth for 19/19 samples |
| OVERALL: No growth in 319 samples including 80 samples from the Isovue multidose, multipatient bottle at the end of 14 hours. | No growth in 80 of 80 samples, including 20 samples from the Isovue multidose, multipatient bottle at the end of 14 hours. | | No growth in 79 of 79 samples, including 20 samples from the Isovue multidose, multipatient bottle at the end of 14 hours. | |

TABLE 4

| Challenge Site | Staphylococcus aureus | | Pseudomonas aeruginosa | |
|---|---|---|---|---|
| Site Description | # Tests | Results | # Tests | Results |
| Center of septum of the bottle cap | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 20 samples | No Growth for 20/20 samples |
| Side surface of the spike guard of the transfer set, around the base of the bottle spike | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 20 samples | No Growth for 20/20 samples |
| The Luer connection of the transfer set | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 20 samples | No Growth for 20/20 samples |
| The exterior base of the syringe tip | 4 replicates of each set: T = 0 hr. T = 4 hr. T = 10 hr. T = 14 hr. Bottle For a total of 20 samples | No Growth for 20/20 samples | 4 replicates of each set: T = 0 hr. T = 4 hr. T = 10 hr. T = 14 hr. Bottle For a total of 20 samples | No Growth for 20/20 samples |
| OVERALL: No growth in 319 samples including 80 samples from the Isovue multidose, multipatient bottle at the end of 14 hours. | No growth in 80 of 80 samples, including 20 samples from the Isovue multidose, multipatient bottle at the end of 14 hours. | | No growth in 80 of 80 samples, including 20 samples from the Isovue multidose, multipatient bottle at the end of 14 hours. | |

The result demonstrated that the Isovue multi-dose, multi-patient container, when used with the Bracco transfer set to fill empty sterile syringes on syringe-based injectors, effectively resisted microbial ingress into the fluidic pathway.

Example 3

Cross-Contamination

A cross-contamination study was performed to verify the ability of a Bracco transfer set similar to that shown in FIG. 3 to avoid cross-contamination between the patient-specific fluid transfer components (identified as the "patient set" in FIG. 3) and the multi-use fluid transfer components (identified as the "day set" in FIG. 3). The Bracco transfer set was configured to transfer medical fluid from multi-dose, multi-patient containers using a fluid pressurization system, such as the Bracco CT Exprès™ system.

To perform the testing, a Bracco CT Exprès™ system was set-up as outlined in the operator's manual. This involved attaching a day set and a patient set to the system as well as installing a multi-dose container of saline. The fluid transfer components of the system, including the day set and patient set, were then primed with saline from the multi-dose container by operating the peristaltic pump of the system to draw fluid from the container and discharge the fluid through the day set and the patient set.

After priming the fluid transfer components, the patient set (PS #1) was ejected from the system and a new patient set (PS #2) was installed and manually primed with saline just past the cassette rollers of the peristaltic pump. The patient set (PS #2) was then clamped adjacent the peristaltic pump and a syringe needle inserted into the patient set tubing, filling the patient set tubing with red no. 40 dye. The distal end of the patient set (PS #2) tubing was then raised to a height 21 cm above the rest of the patient set. The clamp was then opened and the red no. 40 dye allowed to sit in the tubing for 40 minutes, open to atmospheric pressure at the distal end and the peristaltic pump at the opposite end.

After the 40 minute hold time, the patient set tubing was double clamped once just past the peristaltic pump and once approximately 5 cm away from the first clamp. The patient set (PS #2) was then removed from the system and a new patient set (PS #3) installed onto the system. The peristaltic pump was then operated to eject approximately 4 milliliters of solution from each of a first (left side) bottle of contrast, a second (right side) bottle of contrast, and a bag of saline. The samples were collected from the distal end of the patient set (PS #3). In addition, a fourth sample was collected by cutting the removed patient set (PS #2) between the two clamps and extracting fluid from the portion of tube between the clamps.

The samples were analyzed in triplicate at 506 nm to determine if any red no. 40 dye was present in the samples. The results of the cross-contamination testing are provided in Tables 5 and 6 below.

TABLE 5

| Sample ID | Mean Absorbance of Samples [Range is across 9 readings (3 tests (left contrast bottle, right contrast bottle, and saline bag) with 3 readings per test] |
|---|---|
| Replicate 1 | 0.000 [−0.002-0.001] |
| Replicate 2 | −0.001 [−0.002-0.000] |
| Replicate 3 | 0.000 [−0.001-0.001] |
| Replicate 4 | 0.000 [−0.001-0.001] |
| Replicate 5 | 0.000 [0.000-0.000] |
| Replicate 6 | 0.000 [0.000-0.000] |
| Replicate 7 | −0.001 [−0.001-0.000] |
| Replicate 8 | −0.001 [−0.001-0.000] |
| Replicate 9 | 0.000 [0.000-0.001] |
| Replicate 10 | 0.000 [0.000-0.000] |
| Replicate 11 | 0.001 [0.000-0.002] |
| Replicate 12 | 0.001 [0.000-0.002] |
| Replicate 13 | 0.001 [0.001-0.001] |
| Replicate 14 | 0.000 [0.000-0.000] |

TABLE 6

| Sample ID | Mean Absorbance of Challenge Red No. 40 Dye [Range is across 3 readings (1 test in triplicate)] | Calculated Concentration [Concentrated dye was diluted 100,000 fold] |
|---|---|---|
| Replicate 1 | 0.056 [0.055-0.057] | 0.248 |
| Replicate 2 | 0.057 [0.0556-0.058] | 0.253 |
| Replicate 3 | 0.054 [0.053-0.055] | 0.240 |
| Replicate 4 | 0.058 [0.058-0.059] | 0.257 |
| Replicate 5 | 0.059 [0.059-0.059] | 0.262 |
| Replicate 6 | 0.047 [0.047-0.047] | 0.208 |
| Replicate 7 | 0.053 [0.052-0.053] | 0.235 |
| Replicate 8 | 0.054 [0.054-0.055] | 0.240 |
| Replicate 9 | 0.050 [0.050-0.050] | 0.222 |
| Replicate 10 | 0.055 [0.055-0.056] | 0.244 |
| Replicate 11 | 0.056 [0.056-0.057] | 0.248 |
| Replicate 12 | 0.058 [0.058-0.059] | 0.257 |
| Replicate 13 | 0.053 [0.053-0.053] | 0.235 |
| Replicate 14 | 0.041 [0.041-0.042] | 0.182 |
| Average | 0.054 | 0.239 |

The result demonstrated that the Bracco transfer set, when used to dispense fluid from multi-dose, multi-patient containers using the Bracco CT Exprès™ system, effectively resisted cross-contamination between the patient set and the day set.

The invention claimed is:

1. A method comprising:
    applying one or more pathogens to a connection located between a medical fluid container and a fluid pressurizing unit, wherein a fluid transfer set is configured to transfer a fluid from the medical fluid container to the fluid pressurizing unit;
    activating the fluid pressurizing unit multiple times to discharge multiple portions of fluid from the fluid pressurizing unit;
    obtaining a plurality of samples from the multiple portions of fluid discharged from the fluid pressurizing unit, each of the plurality of samples comprising a different portion of fluid; and
    analyzing the plurality of samples to determine a concentration level of the pathogen in the plurality of samples.

2. The method of claim 1, wherein activating the fluid pressurizing unit multiple times to discharge multiple portions of fluid comprises activating the fluid pressurizing unit a first time to discharge a first portion of fluid, ceasing operation of the fluid pressurizing unit, and activating the fluid pressurizing unit a second time to discharge a second portion of fluid.

3. The method of claim 1, wherein analyzing the plurality of samples comprises combining the plurality of samples to form a pooled sample and determining the concentration level of the pathogen in the pooled sample.

4. The method of claim 1, wherein each of the multiple portions of fluid discharged from the fluid pressurizing unit are drawn from a same medical fluid container or set of medical fluid containers connected to the fluid transfer set.

5. The method of claim 1, wherein activating the fluid pressurizing unit multiple times to discharge multiple portions of fluid comprises activating the fluid pressurizing unit a sufficient number of times to empty the medical fluid container and thereby provide an empty medical fluid container, and further comprising replacing the empty medical fluid container with a replacement medical fluid container and further activating the fluid pressurizing unit multiple times to draw fluid from the replacement medical fluid container and discharge multiple portions of fluid from the fluid pressurizing unit.

6. The method of claim 5, further comprising, during replacement of the empty medical fluid container with the replacement medical fluid container, applying the pathogen to the connection located between the replacement medical fluid container and the fluid pressurizing unit.

7. The method of claim 1, wherein at least one of the plurality of samples is obtained from fluid drawn from the medical fluid container and discharged during a first activation of the fluid pressurizing unit, and at least one other of the plurality of samples is obtained from another medical fluid container after replacement of the medical container.

8. The method of claim 1, further comprising, subsequent to applying the pathogen, assembling a fluid delivery system by at least placing the fluid transfer set in fluid communication with the fluid pressurizing unit and the medical fluid container so as to establish fluid communication between the medical fluid container and the fluid pressurizing unit via the fluid transfer set.

9. The method of claim 1, wherein the fluid transfer set comprises a polymeric tube that extends from a proximal end to a distal end and includes a bottle spike positioned on the proximal end of the polymeric tube and a mechanical connector positioned on the distal end of the polymeric tube, and wherein the pressurizing unit comprises a peristaltic pump.

10. The method of claim 1, wherein the connection located between the medical fluid container and the fluid pressurizing unit comprises at least one of a connection between the medical fluid container and the fluid transfer set and a connection between the fluid transfer set and the fluid pressurizing unit.

11. The method of claim 1, wherein the medical fluid container is sized to provide multiple doses of the fluid to multiple different patients.

* * * * *